(12) United States Patent
Seitz et al.

(10) Patent No.: US 7,074,785 B2
(45) Date of Patent: Jul. 11, 2006

(54) Δ¹-PYRROLINES USED AS PESTICIDES

(75) Inventors: Thomas Seitz, Langenfeld (DE);
Martin Füsslein, Düsseldorf (DE);
Johannes Rudolf Jansen, Monheim (DE); Udo Kraatz, Leverkusen (DE);
Christoph Erdelen, deceased, late of Leichlingen (DE); by Angelika Lubos-Erdelen, legal representative, Leichlingen (DE); Andreas Turberg, Haan (DE); Olaf Hansen, Leichlingen (DE)

(73) Assignee: Bayer Cropscience AG, Monheim (DE)

( * ) Notice: Subject to any disclaimer, the term of this patent is extended or adjusted under 35 U.S.C. 154(b) by 13 days.

(21) Appl. No.: 10/489,087

(22) PCT Filed: Sep. 4, 2002

(86) PCT No.: PCT/EP02/09866

§ 371 (c)(1),
(2), (4) Date: Aug. 12, 2004

(87) PCT Pub. No.: WO03/024220

PCT Pub. Date: Mar. 27, 2003

(65) Prior Publication Data

US 2005/0014650 A1 Jan. 20, 2005

(30) Foreign Application Priority Data

Sep. 17, 2001 (DE) .................. 101 45 772

(51) Int. Cl.
*A01N 43/84* (2006.01)
*A01N 43/36* (2006.01)
*C07D 207/20* (2006.01)
*C07D 413/12* (2006.01)
*C07D 413/10* (2006.01)

(52) U.S. Cl. .................. 514/235.5; 514/326; 514/422; 514/429; 514/376; 514/343; 514/252.05; 514/255.05; 514/256; 544/141; 544/238; 544/333; 544/405; 546/208; 546/276.4; 548/229; 548/231; 548/517; 548/518; 548/527; 548/565

(58) Field of Classification Search ................ 548/565, 548/229, 517, 518, 527; 546/208; 544/141; 514/429, 326, 235.5, 376, 422

See application file for complete search history.

(56) References Cited

U.S. PATENT DOCUMENTS 6,489,490 B1 12/2002 Plant et al.
6,599,924 B1 7/2003 Plant et al.
6,632,833 B1 10/2003 Mencke et al.

FOREIGN PATENT DOCUMENTS

| CH | 490 012 | 5/1970 |
| JP | 2000-290265 | 10/2000 |
| WO | 98/22438 | 5/1998 |
| WO | 02/46151 | 6/2002 |
| WO | 02/064588 | 8/2002 |

OTHER PUBLICATIONS

Tetrahedron Lett., 38, (month unavailable) 1997, pp. 3841-3844, André Giroux, Yongxin Han and Petpiboon Prasit, One Pot Biarly Synthesis *via in situ* Boronate Formation.

Syn. Commun., 15 (month unavailable) 1985, pp. 1025-1031, Stanley Raucher & David S. Jones, "A Convenient Method for the Conversion of Amines to Carbamates".

J. Org. Chem., 60, (month unavailable) 1995, pp. 7508-7510, Tatsuo Ishiyama, Miki Murata, and Norio Miyaura, Palladium(0)-Catalyzed Cross-Coupling Reaction of Alkoxydiboron with Haloarenes: A Direct Procedure for Arylboronic Esters.

Tetrahedron Lett., 38, (month unavailable) 1997, pp. 3447-3450, Tatsuo Ishiyama, Yoshiya Itoh, Takahiro Kitano, and Norio Miyaura, "Synthesis of Arylboronates *via* the Palladium(0)-Catalyzed Cross-Coupling Reaction of Tetra(alkoxo)diborons with Aryl Triflates".

Tetrahedron Lett., 36, (month unavailable) 1995, pp. 9085-9088, Stephen A. Hitchcock, Daniel R. Mayhugh and G. Stuart Gregory, Selectivity in Palladium(0)-Catalyzed Cross-Coupling Reactions: Application to a Tandem Stille Reaction.

(Continued)

*Primary Examiner*—Emily Bernhardt
(74) *Attorney, Agent, or Firm*—Richard E. L. Henderson

(57) ABSTRACT

Novel Δ¹-pyrrolines of the formula (I)

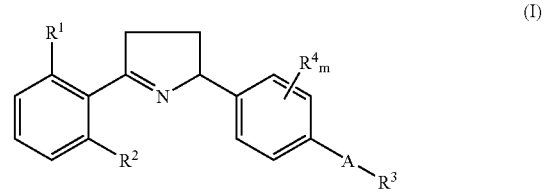

in which
$R^1$, $R^2$, $R^3$, A, $R^4$ and m have the meanings given in the description,
a number of processes for preparing these substances, and their use for controlling pests, and also novel intermediates and their preparation.

25 Claims, No Drawings

OTHER PUBLICATIONS

Tetrahedron Asymmetry 9, (month unavailable) 1998, pp. 1035-1042, Ayhan S. Demir, Cihangir Tanyeli, Ali Cagir, M. Nawaz Tahir and Dincer Ulku, "Novel enantioselective synthesis of *trans*-α-(2-carboxcycloprop-1-yl)glycines: conformationally constrained L-glutamate analogues".

J. Org. Chem., vol. 43, (month unavailable) 1978, pp. 4593-4596, Georg A. Dilbeck, Lamar Field, August A. Gallo and Robert J. Gargiulo, Biologically Oriented Organic Sulfur Chemistry, 19. Synthesis and Properties of 2-Amino-5-mercapto-5-methylhexanoic Acid, a Bishomologue of Penicillamine. Use of Boron Trifluoride Etherate for Catalyzing Markownikoff Addition of a Thiol to an Olefin.

J. Chem. Soc., (month unavailable) 1964, pp. 4142-4146, T. Kametani and K. Ogasawara, Cularine and Related Compounds, Part VIII. A Modified Total Synthesis of (±) Cularine Methiodide.

J. Org. Chem., 43, (month unavailable) 1978, pp. 3711-3713, Dennis D. Keith, John Tortora, and Roxana Yang, "Synthesis of L-2-Amino-4-methoxy-*trans*-but 3-enoci Acid".

Appl. Microbiol Biotechnol., 47, (month unavailable) 1997, pp. 650-657, M. Graf, A. Brunella, M. Kittelmann, K. Laumen, O. Ghisalba, "Isolation and characterization of highly (R)-specific N-acetyl-1-phenylethylamine amidohydrolase, a new enzyme from *Arthrobacter aurescens* AcR5b".

Protective Groups in Organic Synthesis (month unavailable) 1999, pp. 553-555, T.W. Greene, P.G.M. Wuts, "Amides".

Chem. Ind., 37, (month unavailable) 1985, pp. 730-732, Harry R. Ungerer, "Schiffsfarben—eine Spezialität der seenahen Lackindustrie".

Tetrahedron Letters, vol. 25, (month unavailable) 1984, pp. 557-578, Romulado Caputo, Carla Ferreri, Giovanni Palumbo, "Trimethylsilyl Tetrafluoroborate A Convenient Reagent For Solvolysis Reactions".

Δ¹-PYRROLINES USED AS PESTICIDES

The present patent application has been filed under 35 U.S.C. 371 as a national stage application of PCT/EP02/09866, filed Sep. 4, 2002, which was published in German as International Patent Publication WO 03/024220 on Mar. 27, 2003, which is entitled to the right of priority of German Patent Application 101 45 772.3, filed Sep. 17, 2001.

The present invention relates to novel Δ¹-pyrrolines, to a number of processes for preparing them and to their use as pesticides.

It is already known that numerous Δ¹-pyrrolines possess insecticidal properties (cf. WO 00/21958, WO 99/59968, WO 99/59967 and WO 98/22438). The activity of these substances is good, but still leaves something to be desired in some cases.

This invention now provides novel Δ¹-pyrrolines of the formula (I)

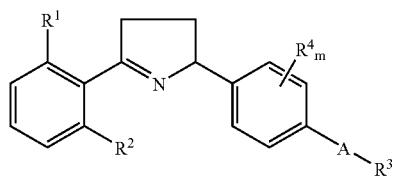

in which
R¹ represents halogen or methyl,
R² represents hydrogen or halogen,
R³ represents —N(R⁶)—C(=Y)—X—R⁷, and
a) A represents arylene or 5-membered heteroarylene having 1 to 3 heteroatoms, containing 0 to 3 nitrogen atoms, 0 to 1 oxygen atom and/or 0 to 1 sulphur atom, or 6-membered heteroarylene having 3 nitrogen atoms or 6-membered heteroarylene having 1 nitrogen atom and 1 to 2 further heteroatoms, of which 0 to 2 may be oxygen atoms and/or 0 to 2 may be sulphur atoms, each arylene or heteroarylene being optionally substituted from one to four times by identical or different substituents R⁵, and
Y represents O (oxygen) or S (sulphur), and
X represents O (oxygen), S (sulphur) or NR⁸, or
b) A represents pyridinylene, pyrimidinylene, pyrazinylene or pyridazinylene each optionally substituted once or twice by identical or different substituents R⁵, and
Y represents O (oxygen) or S (sulphur), and
X represents S (sulphur) or NR⁸, or
c) A represents pyridinylene, pyrimidinylene, pyrazinylene or pyridazinylene each optionally substituted once or twice by identical or different substituents R⁵, and
Y represents S (sulphur), and
X represents O (oxygen), or
d) A represents pyridinylene, pyrimidinylene, pyrazinylene or pyridazinylene each optionally substituted once or twice by identical or different substituents R⁵, and
Y represents O (oxygen), and
X represents O (oxygen), and
R⁴ and R⁵ independently of one another represent halogen, alkyl, alkoxy, alkylthio, haloalkyl, haloalkoxy or haloalkylthio,
m represents 0, 1, 2, 3 or 4,
R⁶ represents hydrogen or alkyl,
R⁷ and R⁸ independently of one another represent hydrogen or represent alkyl or alkenyl each optionally substituted one or more times by identical or different substituents selected from the group consisting of halogen, alkylcarbonyl, alkylcarbonyloxy, alkylamino, dialkylamino, alkoxy, alkylthio, alkoxyalkoxy, haloalkoxy, haloalkylthio and halogenalkoxyalkoxy;
or represent cycloalkyl, cycloalkylalkyl, aryl, arylalkyl, saturated or unsaturated 5- to 10-membered heterocyclyl or heterocyclylalkyl each of which is optionally substituted one or more times by identical or different substitutents selected from the group consisting of halogen, alkyl, haloalkyl, alkoxy, haloalkoxy, alkylthio, haloalkylthio, alkylcarbonyl and alkoxycarbonyl,
R⁶ and R⁷ further together represent alkylene optionally substituted one or more times by alkyl, or
R⁷ and R⁸ further, together with the nitrogen atom to which they are attached, represent a saturated or unsaturated 5- to 10-membered heterocycle which may optionally contain a further heteroatom group from the series —O—, —S— and —NR⁹— and which may optionally be substituted one or more times by identical or different substituents selected from the group consisting of halogen, alkyl, alkoxy, alkylthio, haloalkyl, haloalkoxy and haloalkylthio, and
R⁹ represents hydrogen, alkyl or alkenyl.

Where appropriate, depending on the nature and number of the substituents, the compounds of the formula (I) may be in the form of geometrical and/or optical isomers, regioisomers or configurational isomers, or isomer mixtures thereof in varying compositions. The pure isomers and the isomer mixtures are claimed in accordance with the invention.

It has also been found that Δ¹-pyrrolines of the formula (I) may be prepared by
A) reacting Δ¹-pyrrolines of the formula (II)

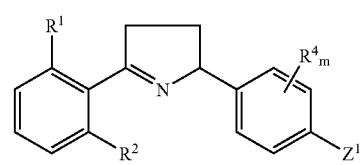

in which
R¹, R², R⁴ and m have the meanings given above and
Z¹ represents chlorine, bromine, iodine, —OSO₂CF₃ or —OSO₂(CF₂)₃CF₃, in a tandem reaction with (hetero)cycles of the formula (III)

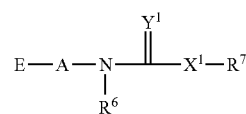

in which
A, R⁶ and R⁷ have the meanings given above,
Y¹ represents O (oxygen),
X¹ represents O (oxygen) or NR⁸,
E represents chlorine, bromine, iodine, —OSO₂CF₃ or —OSO₂(CF₂)₃CF₃,
in the presence of a catalyst, in the presence of a diboronic ester and, where appropriate, in the presence of an acid binder and, where appropriate, in the presence of a diluent, or
B) reacting Δ¹-pyrrolines of the formula (IV)

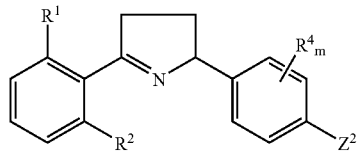

(IV)

in which
R¹, R², R⁴ and m have the meanings given above,
Z² represents —B(OH)₂, (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl,
with (hetero)cycles of the formula (III)

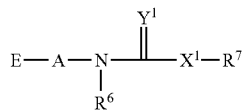

(III)

in which
E, A, Y¹, X¹, R⁶ and R⁷ have the meanings given above,
in the presence of a catalyst, where appropriate in the presence of an acid binder and, where appropriate, in the presence of a diluent, or
C) reacting Δ¹-pyrrolines of the formula (II)

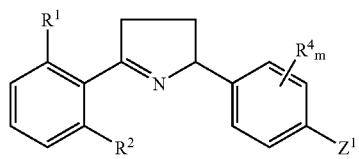

(II)

in which
R¹, R², R⁴, m and Z¹ have the meanings given above with boronic acid derivatives of the formula (V)

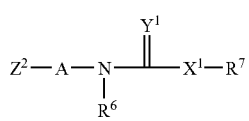

(V)

in which
Z², A, Y¹, X¹, R⁶ and R⁷ have the meanings given above in the presence of a catalyst, where appropriate in the presence of an acid binder and, where appropriate, in the presence of a diluent, or
D) reacting Δ¹-pyrrolines of the formula (II-a)

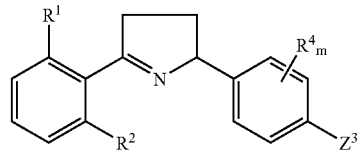

(II-a)

in which
R¹, R², R⁴ and m have the meanings given above,
Z³ represents bromine or iodine with organometallic compounds of the formula (VI)

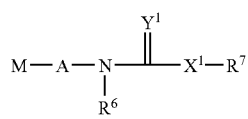

(VI)

in which
A, Y¹, X¹, R⁶ and R⁷ have the meanings given above,
M represents ZnCl, Sn(Me)₃ or Sn(n-Bu)₃,
in the presence of a catalyst, where appropriate in the presence of an acid binder and, where appropriate, in the presence of a diluent, or
E) reacting Δ¹-pyrrolines of the formula (VII)

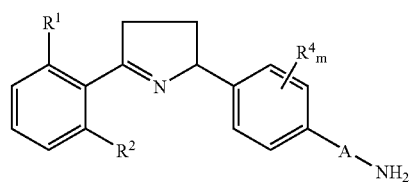

(VII)

in which
R¹, R², A, R⁴ and m have the meanings given above either with an iso(thio)cyanate of the formula (VIII)

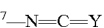

R⁷—N=C=Y       (VIII)

in which
Y and R⁷ have the meanings given above or with a (thio)carbonate of the formula (IX)

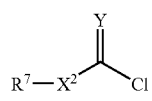

(IX)

in which

Y and $R^7$ have the meanings given above, $X^2$ represents O (oxygen) or S (sulphur), in each case where appropriate in the presence of a diluent and, where appropriate, in the presence of an acid binder.

Finally it has been found that the compounds of the formula (I) according to the invention possess very good insecticidal properties and may be used both in crop protection and in the protection of materials for the purpose of controlling unwanted pests, such as insects.

The formula (I) provides a general definition of the $\Delta^1$-pyrrolines according to the invention.

Preferred compounds of the formula (I) are those in which $R^1$ represents fluorine, chlorine, bromine or methyl, $R^2$ represents hydrogen, fluorine, chlorine or bromine, $R^3$ represents —$N(R^6)$—$C(=Y)$—$X$—$R^7$, and a) A represents arylene (especially phenylene) or 5-membered heteroarylene having 1 to 3 heteroatoms, containing 0 to 3 nitrogen atoms, 0 to 1 oxygen atom and/or 0 to 1 sulphur atom (in particular from the series pyrrolylene, furylene, thienylene, pyrazylene, imidazylene, triazylene, thiazylene or oxazylene), or 6-membered heteroarylene having 3 nitrogen atoms (especially triazinylene) or 6-membered heteroarylene having 1 nitrogen atom and 1 to 2 further heteroatoms, of which 0 to 2 may be oxygen atoms and/or 0 to 2 may be sulphur atoms (in particular from the series oxazinylene or thiazinylene), each being optionally substituted from one to three times by identical or different substituents $R^5$, and Y represents O (oxygen) or S (sulphur) and X represents O (oxygen), S (sulphur) or $NR^8$, or b) A represents pyridinylene, pyrimidinylene, pyrazinylene or pyridazinylene each optionally substituted once or twice by identical or different substituents $R^5$, and Y represents O (oxygen) or S (sulphur), and X represents S (sulphur) or $NR^8$, or c) A represents pyridinylene, pyrimidinylene, pyrazinylene or pyridazinylene each optionally substituted once or twice by identical or different substituents $R^5$, and Y represents S (sulphur), and X represents O (oxygen), or d) A represents pyridinylene, pyrimidinylene, pyrazinylene or pyridazinylene each optionally substituted once or twice by identical or different substituents $R^5$, and Y represents O (oxygen), and X represents O (oxygen), and $R^4$ and $R^5$ independently of one another represents fluorine, chlorine, bromine, $C_1$–$C_6$-alkyl, $C_1$–$C_6$-alkoxy, $C_1$–$C_6$-alkylthio, $C_1$–$C_6$-haloalkyl, $C_1$–$C_6$-haloalkoxy or $C_1$–$C_6$-haloalkylthio, m represents 0, 1, 2 or 3, $R^6$ represents hydrogen or $C_1$–$C_6$-alkyl, $R^7$ and $R^8$ independently of one another represent hydrogen or represent $C_1$–$C_{20}$-alkyl or $C_2$–$C_{20}$-alkenyl each optionally substituted one or more times by identical or different substituents selected from the group consisting of fluorine, chlorine, bromine, $C_1$–$C_6$-alkylcarbonyl, $C_1$–$C_6$-alkylcarbonyloxy, $C_1$–$C_6$-alkylamino, di-($C_1$–$C_6$-alkyl) amino, $C_1$–$C_{10}$-alkoxy, $C_1$–$C_{10}$-alkylthio, $C_1$–$C_{10}$-alkoxy-$C_1$–$C_{10}$-alkoxy, $C_1$–$C_{10}$-haloalkoxy, $C_1$–$C_{10}$-haloalkylthio and $C_1$–$C_{10}$-haloalkoxy-$C_1$–$C_{10}$-alkoxy;

or represent $C_3$–$C_{12}$-cycloalkyl, $C_3$–$C_7$-cycloalkyl-$C_1$–$C_4$-alkyl, aryl, aryl-$C_1$–$C_4$-alkyl, saturated or unsaturated 5- to 10-membered heterocyclyl or heterocyclyl-$C_1$–$C_4$-alkyl having 1 to 4 heteroatoms, containing 0 to 4 nitrogen atoms, 0 to 2 non-adjacent oxygen atoms and/or 0 to 2 non-adjacent sulphur atoms (especially tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl) each optionally substituted from one to four times by identical or different substituents selected from the group consisting of fluorine, chlorine, bromine, $C_1$–$C_6$-alkyl, $C_1$–$C_6$-alkoxy, $C_1$–$C_6$-alkylthio, $C_1$–$C_6$-haloalkyl, $C_1$–$C_6$-haloalkoxy, $C_1$–$C_6$-haloalkylthio, $C_1$–$C_6$-alkylcarbonyl and $C_1$–$C_6$-alkoxycarbonyl, $R^6$ and $R^7$ further together represent $C_2$–$C_4$-alkylene optionally substituted from one to four times by $C_1$–$C_4$-alkyl, or $R^7$ and $R^8$ further represent, together with the nitrogen atom to which they are attached, a saturated or unsaturated 5- to 10-membered heterocycle which may optionally contain a further heteroatom group from the series —O—, —S— or —$NR^9$— and which may optionally be substituted from one to four times by identical or different substituents selected from the group consisting of fluorine, chlorine, bromine, $C_1$–$C_6$-alkyl, $C_1$–$C_6$-alkoxy, $C_1$–$C_6$-alkylthio, $C_1$–$C_6$-haloalkyl, $C_1$–$C_6$-haloalkoxy and/or $C_1$–$C_6$-haloalkylthio, and $R^9$ represents hydrogen, $C_1$–$C_6$-alkyl or $C_2$–$C_6$-alkenyl.

Particularly preferred compounds of the formula (I) are those in which $R^1$ represents fluorine, chlorine or methyl, $R^2$ represents hydrogen, fluorine or chlorine, $R^3$ represents —$N(R^6)$—$C(=Y)$—$X$—$R^7$, and a) A represents phenylene, pyrrolylene, furylene, thienylene, pyrazylene, imidazylene, triazylene, thiazylene or oxazylene each optionally substituted once or twice by identical or different substituents $R^5$, and Y represents O (oxygen) or S (sulphur), and X represents O (oxygen), S (sulphur) or $NR^8$, or b) A represents pyridinylene, pyrimidinylene, pyrazinylene or pyridazinylene each optionally substituted once or twice by identical or different substituents $R^5$, and Y represents O (oxygen) or S (sulphur), and X represents S (sulphur) or $NR^8$, or c) A represents pyridinylene, pyrimidinylene, pyrazinylene or pyridazinylene each optionally substituted once or twice by identical or different substituents $R^5$, and Y represents S (sulphur), and X represents O (oxygen), or d) A represents pyridinylene, pyrimidinylene, pyrazinylene or pyridazinylene each optionally substituted once or twice by identical or different substituents $R^5$, and Y represents O (oxygen), and X represents O (oxygen), and R$^4$ and R$^5$ independently of one another represent fluorine, chlorine, C$_1$–C$_4$-alkyl, C$_1$–C$_4$-alkoxy, C$_1$–C$_4$-alkylthio; C$_1$–C$_4$-haloalkyl, C$_1$–C$_4$-haloalkoxy or C$_1$–C$_4$-haloalkylthio having in each case 1 to 9 fluorine, chlorine and/or bromine atoms, m represents 0, 1 or 2, R$^6$ represents hydrogen or C$_1$–C$_4$-alkyl, R$^7$ and R$^8$ independently of one another represent hydrogen or represent C$_1$–C$_{16}$-alkyl or C$_2$–C$_{16}$-alkenyl each optionally substituted one or more times by identical or different substituents selected from the group consisting of fluorine, chlorine, bromine, C$_1$–C$_4$-alkylcarbonyl, C$_1$–C$_4$-alkylcarbonyloxy, C$_1$–C$_4$-alkylamino, di-(C$_1$–C$_4$-alkyl) amino, C$_1$–C$_{10}$-alkoxy, C$_1$–C$_{10}$-alkylthio, C$_1$–C$_{10}$-alkoxy-C$_1$–C$_6$-alkoxy, C$_1$–C$_{10}$-haloalkoxy, C$_1$–C$_{10}$-haloalkylthio and C$_1$–C$_{10}$-haloalkoxy-C$_1$–C$_6$-alkoxy having in each case 1 to 21 fluorine, chlorine and/or bromine atoms;

or represent C$_3$–C$_{10}$-cycloalkyl, C$_3$–C$_6$-cycloalkyl-C$_1$–C$_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl each optionally substituted from one to three times by identical or different substituents selected from the group consisting of fluorine, chlorine, bromine, C$_1$–C$_4$-alkyl, C$_1$–C$_4$-alkoxy, C$_1$–C$_4$-alkylthio, C$_1$–C$_4$-haloalkyl, C$_1$–C$_4$-haloalkoxy, C$_1$–C$_4$-haloalkylthio having in each case 1 to 9 fluorine, chlorine and/or bromine atoms, C$_1$–C$_4$-alkylcarbonyl and C$_1$–C$_4$-alkoxycarbonyl, R$^6$ and R$^7$ further together represent C$_2$–C$_3$-alkylene optionally substituted from one to three times by C$_1$–C$_4$-alkyl, or R$^7$ and R$^8$ further represent, together with the nitrogen atom to which they are attached, a saturated or unsaturated 5- to 7-membered heterocycle which may optionally contain a further heteroatom group from the series —O—, —S— or —NR$^9$— (in particular from the series piperidino, morpholino, thiomorpholino, piperazino, pyrrolidino, oxazolidino, thiazolidino, 4H-1-oxazinyl, 4H-1-thiazinyl) and which may optionally be substituted from one to four times by identical or different substituents selected from the group consisting of fluorine, chlorine, C$_1$–C$_4$-alkyl, C$_1$–C$_4$-alkoxy, C$_1$–C$_4$-alkylthio, C$_1$–C$_4$-haloalkyl, C$_1$–C$_4$-haloalkoxy and/or C$_1$–C$_4$-haloalkylthio having in each case 1 to 9 fluorine, chlorine and/or bromine atoms, and R$^9$ represents hydrogen, C$_1$–C$_4$-alkyl or C$_2$–C$_4$-alkenyl.

Very particularly preferred compounds of the formula (I) are those in which

R$^1$ represents fluorine or chlorine,

R$^2$ represents hydrogen or fluorine,

R$^3$ represents —N(R$^6$)—C(=Y)—X—R$^7$, and a) A represents 1,2-phenylene, 1,4-phenylene, 2,5-pyrrolylene, 2,5-furylene, 2,4-furylene, 2,5-thienylene, 2,4-thienylene, 2,5-thiazylene, 2,4-thiazylene, 2,5-oxazylene or 2,4-oxazylene each optionally substituted once by R$^5$, and Y represents O (oxygen) or S (sulphur), and
X represents O (oxygen), S (sulphur) or NR$^8$, or b) A represents 2,5-pyridinylene, 2,5-pyrimidinylene, 2,5-pyrazinylene or 3,6-pyridazinylene each optionally substituted once by R$^5$, and
Y represents O (oxygen) or S (sulphur), and
X represents S (sulphur) or NR$^8$, or c) A represents 2,5-pyridinylene, 2,5-pyrimidinylene, 2,5-pyrazinylene or 3,6-pyridazinylene each optionally substituted once by R$^5$, and
Y represents S (sulphur), and
X represents O (oxygen), or d) A represents 2,5-pyridinylene, 2,5-pyrimidinylene, 2,5-pyrazinylene or 3,6-pyridazinylene each optionally substituted once by R$^5$, and
Y represents O (oxygen), and
X represents O (oxygen), and R$^4$ and R$^5$ independently of one another represent fluorine, chlorine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, methylthio, ethylthio, n-propylthio, i-propylthio, n-butylthio, i-butylthio, s-butylthio, t-butylthio, trifluoromethyl, trifluoroethyl, trifluoromethoxy, trifluoroethoxy, trifluoromethylthio or trifluoroethylthio, m represents 0 or 1, R$^6$ represents hydrogen, methyl, ethyl, n-propyl, i-propyl, n-butyl, i-butyl, s-butyl or t-butyl, R$^7$ and R$^8$ independently of one another represent hydrogen or represent C$_1$–C$_{10}$-alkyl or C$_2$–C$_{10}$-alkenyl (especially methyl, ethyl, n-propyl, i-propyl, n-butyl, i-butyl, s-butyl, t-butyl, the isomeric pentyls, the isomeric hexyls) each optionally substituted one or more times by identical or different substituents selected from the group consisting of fluorine, chlorine, bromine, C$_1$–C$_4$-alkylcarbonyl, C$_1$–C$_4$-alkylcarbonyloxy, C$_1$–C$_4$-alkylamino, di-(C$_1$–C$_4$-alkyl)amino, C$_1$–$_{10}$-alkoxy, C$_1$–C$_8$-alkoxy-C$_1$–C$_6$-alkoxy, C$_1$–C$_{10}$-alkylthio, C$_1$–C$_{10}$-haloalkoxy, C$_1$–C$_{10}$-haloalkylthio having in each case 1 to 21 fluorine, chlorine and/or bromine atoms, C$_1$–C$_8$-haloalkoxy-C$_1$–C$_6$-alkoxy having 1 to 17 fluorine, chlorine and/or bromine atoms;

or represent C$_3$–C$_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl each optionally substituted from one to three times by identical or different substituents selected from the group consisting of fluorine, chlorine, bromine, C$_1$–C$_4$-alkyl, C$_1$–C$_4$-alkoxy, C$_1$–C$_4$-alkylthio, C$_1$–C$_4$-haloalkyl, C$_1$–C$_4$-haloalkoxy, C$_1$–C$_4$-haloalkylthio having in each case 1 to 9 fluorine, chlorine and/or bromine atoms, C$_1$–C$_4$-alkylcarbonyl and C$_1$–C$_4$-alkoxycarbonyl, R$^6$ and R$^7$ together further represent methylene or ethylene each optionally substituted once or twice by identical or different methyl, ethyl, n-propyl or i-propyl substituents, or R[7] and R[8] further represent, together with the nitrogen atom to which they are attached, a 5- to 6-membered heterocycle from the series piperidino, morpholino, thiomorpholino, piperazino, pyrrolidino, oxazolidino, thiazolidino, 4H-1-oxazinyl, 4H-1-thiazinyl which may optionally be substituted from one to four times by identical or different substituents selected from the group consisting of fluorine, chlorine, bromine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, methylthio, ethylthio, n-propylthio, i-propylthio, n-butylthio, i-butylthio, s-butylthio, t-butylthio, $C_1$–$C_4$-haloalkyl, $C_1$–$C_4$-haloalkoxy, $C_1$–$C_4$-haloalkylthio having in each case 1 to 9 fluorine, chlorine and/or bromine atoms, the piperazino radical being substituted on the second nitrogen atom by R[9], and R[9] represents hydrogen, methyl, ethyl, n-propyl, i-propyl, n-butyl, i-butyl, s-butyl, t-butyl, vinyl or allyl.

Further very particularly preferred compounds are those of the formulae (I-1) and (I-2)

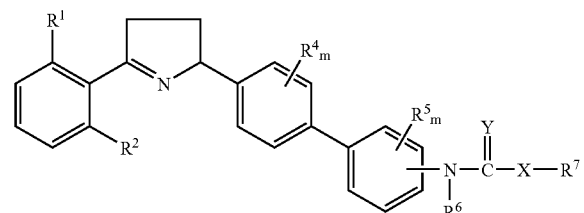

(I-1)

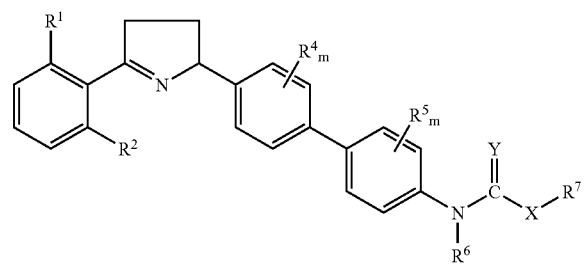

(I-2)

in each of which
a) Y represents O (oxygen) or S (sulphur), and
X represents O (oxygen), S (sulphur) or NR[8], and R[1], R[2], R[4], R[5], m, R[6], R[7], R[8] have the meanings given above.

In the formulae (I-1) and (I-2) the radicals R[1], R[2], R[4], R[5], m, R[6], R[7], R[8] each represent with preference, with particular preference or with very particular preference those definitions stated as being preferred, particularly preferred, etc. for these radicals in the context of the description of the substances of the formula (I) according to the invention. Y and X represent in each case with preference, with particular preference or with very particular preference those definitions described in each case under the corresponding section "a)".

Further very particularly preferred compounds are those of the formulae (I-3) to (I-8)

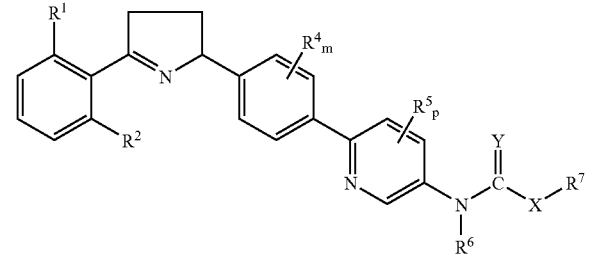

(I-3)

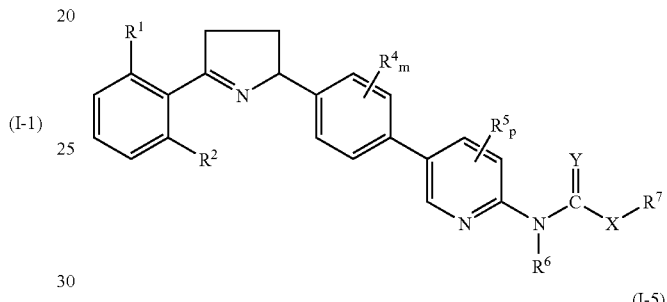

(I-4)

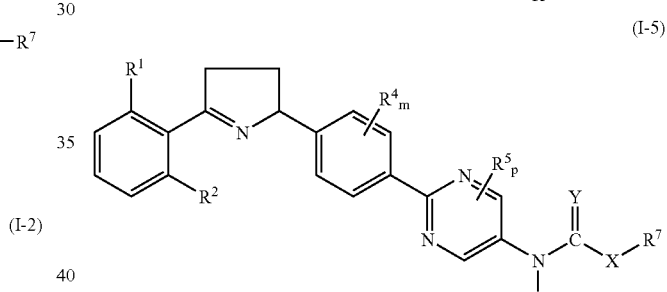

(I-5)

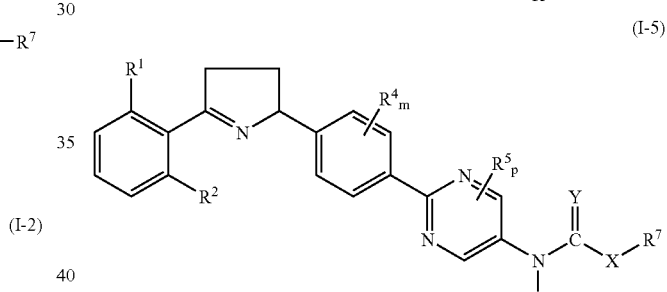

(I-6)

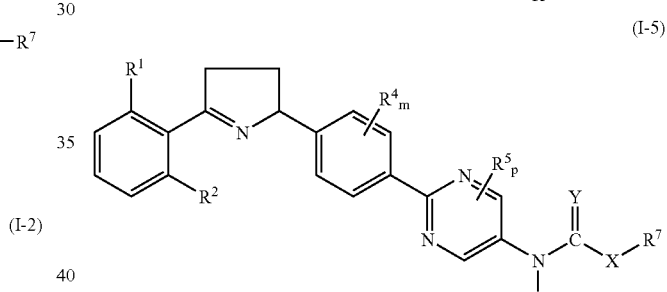

(I-7)

-continued (I-8)

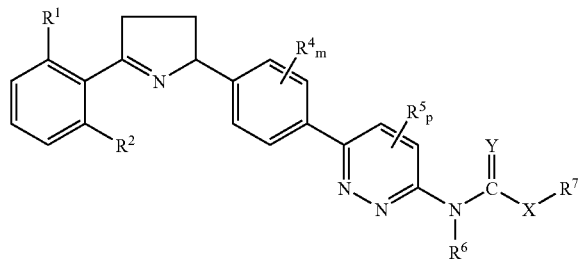

in each of which
p represents 0, 1 or 2,
b) Y represents O (oxygen) or S (sulphur), and
   X represents S (sulphur) or NR$^8$,
or
c) Y represents S (sulphur), and
   X represents O (oxygen),
or
d) Y represents O (oxygen), and
   X represents O (oxygen),
and R$^1$, R$^2$, R$^4$, R$^5$, m, R$^6$, R$^7$ and R$^8$ have the meanings given above.

In the formulae (I-3) to (I-8) the radicals R$^1$, R$^2$, R$^4$, R$^5$, m, R$^6$, R$^7$, R$^8$ each represent with preference, with particular preference or with very particular preference those definitions stated as being preferred, particularly preferred, etc. for these radicals in the context of the description of the substances of the formula (I) according to the invention. Y and X represent in each case with preference, with particular preference or with very particular preference those definitions described in each case under the corresponding section "a)", "b)", "c)" and "d)". p represents preferably 0, 1 or 2, with particular preference 0 or 1, with very particular preference 0.

Further preferred compounds of the formula (I) are those in which A represents phenylene, preferably 1,4-phenylene.

Further preferred compounds of the formula (I) are those in which A represents pyridinylene, pyrimidinylene, pyrazinylene or pyridazinylene, preferably 2,5-pyridinylene, 2,5-pyrimidinylene, 2,5-pyrazinylene or 3,6-pyridazinylene.

Further preferred compounds of the formula (I) are those in which Y represents O (oxygen).

Further preferred compounds of the formula (I) are those in which X represents O (oxygen) or NR$^8$, preferably O (oxygen).

Further preferred compounds of the formula (I) are those in which Y and X each represent O (oxygen).

Further preferred compounds of the formula (I) are those in which Y represents O (oxygen) and X represents NR$^8$.

Further preferred compounds of the formula (I) are those in which A represents phenylene, preferably 1,4-phenylene, Y represents O (oxygen) or S (sulphur), preferably O (oxygen), and X represents O (oxygen), S (sulphur) or NR$^8$, preferably O (oxygen) or NR$^8$, with particular preference O (oxygen).

Further preferred compounds of the formula (I) are those in which R$^1$ and R$^2$ each represents fluorine.

Further preferred compounds of the formula (I) are those in which R$^1$ represents methyl and R$^2$ represents hydrogen.

Further preferred compounds of the formula (I) are those in which R$^1$ represents chlorine and R$^2$ represents hydrogen.

Further preferred compounds of the formula (I) are those in which R$^1$ represents chlorine and R$^2$ represents fluorine.

Further preferred compounds of the formula (I) are those in which R$^6$ represents hydrogen.

Further preferred compounds of the formula (I-a) are those with (R) configuration in position 5 of the pyrroline ring.

(I-a)

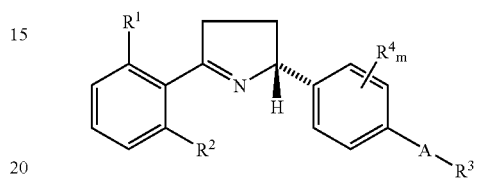

in which
R$^1$, R$^2$, A, R$^3$, R$^4$ and m have the meanings given above.

In accordance with formula (I-a), the compounds (I-1) to (I-8) may also be present with R configuration in position 2 of the 2H-pyrrole (corresponding to position 5 when named as pyrroline).

Compounds of the formula (I-a) are obtained by customary methods of optical resolution, such as, for example, by chromatographing the corresponding racemates on a chiral stationary phase. It is possible to separate either the racemic end products or racemic intermediates in this way into the two enantiomers.

Saturated hydrocarbon radicals such as alkyl, alone or in conjunction with heteroatoms, such as in alkoxy, for example, may where possible in each case be straight-chain or branched.

The radical definitions and elucidations set out above in general or in ranges of preference may, however, also be combined as desired with one another, i.e. are arbitrary combinations between the respective ranges and ranges of preference. They apply both to the end products and to the precursors and intermediates accordingly.

Using 5-(2,6-difluorophenyl)-2-(4-bromophenyl)-3,4-dihydro-2H-pyrrole, methyl 4-bromophenylcarbamate and 4,4,4',4',5,5,',5'-octamethyl-2,2'-bis-1,3,2-dioxaborolane as starting materials and a palladium catalyst, the course of the process (A) according to the invention can be illustrated by the following equation.

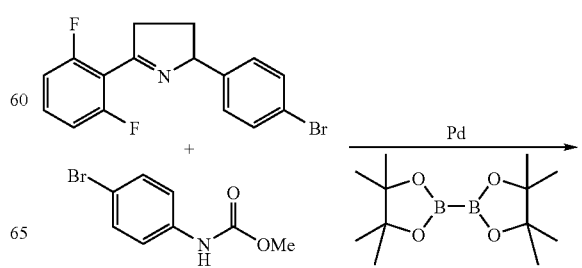

-continued

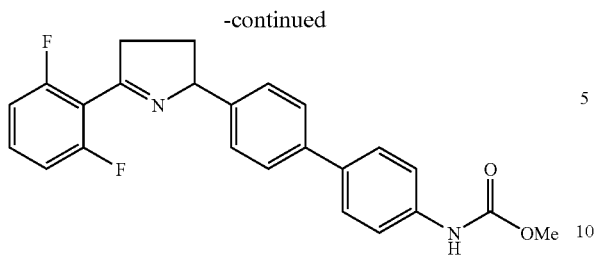

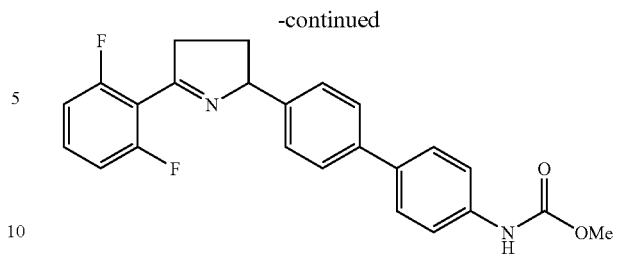

Using 5-(2,6-difluorophenyl)-2-[4-(4,4,5,5-tetramethyl-1,3,2-dioxaborolan-2-yl)-phenyl]-3,4-dihydro-2H-pyrrole and methyl 4-bromophenylcarbamate as starting materials and a palladium catalyst, the course of the process (B) according to the invention can be illustrated by the following equation.

Using 5-(2,6-difluorophenyl)-2-(4-bromophenyl)-3,4-dihydro-2H-pyrrole and methyl 4-(tributylstannyl)phenylcarbamate as starting materials and a palladium catalyst, the course of the process (D) according to the invention can be illustrated by the following equation.

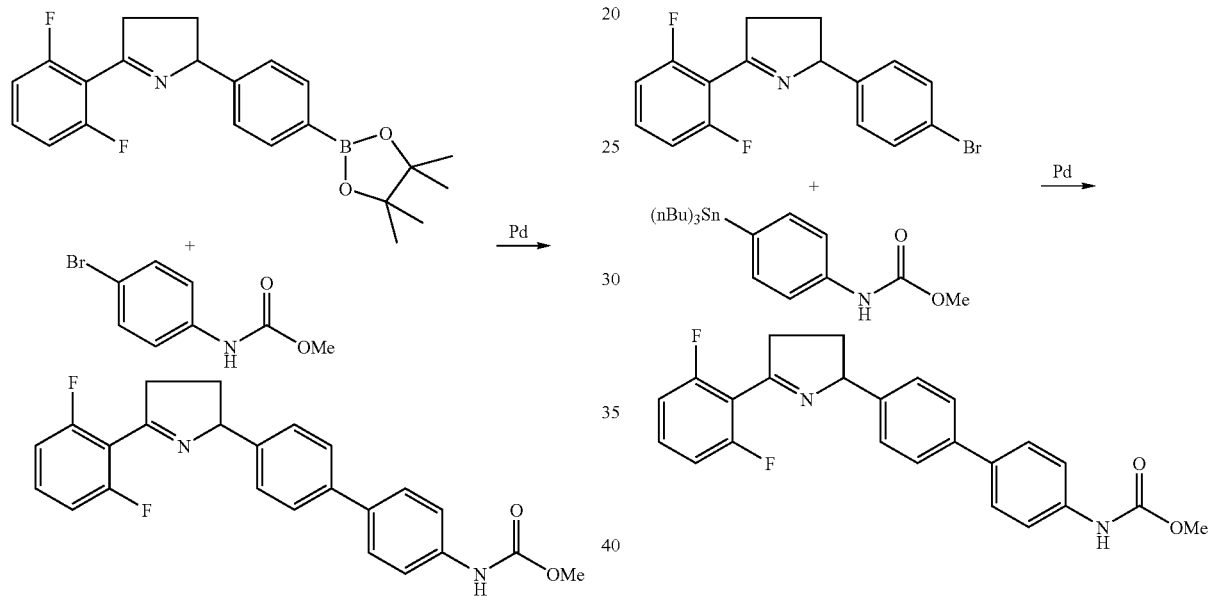

Using 5-(2,6-difluorophenyl)-2-[4-(trifluoromethylsulfonyloxy)phenyl]-3,4-dihydro-2H-pyrrole and methyl 4-(4,4,5,5-tetramethyl-1,3,2-dioxaborolan-2-yl)phenylcarbamate as starting materials and a palladium catalyst, the course of the process (C) according to the invention can be illustrated by the following equation.

Using 4'-[5-(2,6-difluorophenyl)-3,4-dihydro-2H-pyrrol-2-yl]-1,1'-biphenyl-4-amine and (methylimino)(thioxo)methane as starting material, the course of the process (E) according to the invention can be illustrated by the following equation.

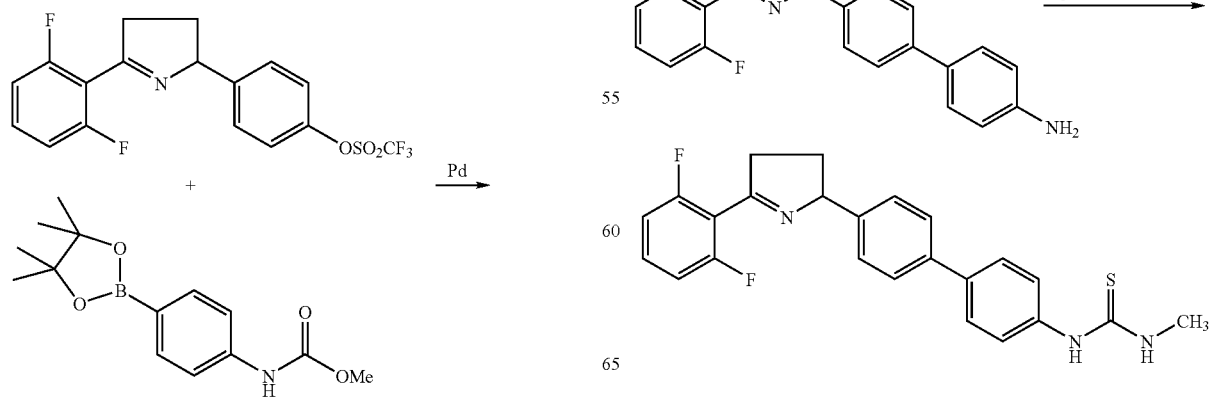

Elucidation of the Processes and Intermediates

Process (A)

In a first reaction step, a compound of the formula (II) is coupled with a diboronic acid ester in the presence of a palladium catalyst, if appropriate in the presence of an acid binder and if appropriate in the presence of a solvent. Without any isolation of the intermediate, a compound of the formula (III) is coupled in the same reaction vessel in a second reaction step in the presence of a catalyst, if appropriate in the presence of an acid binder and if appropriate in the presence of a solvent (cf., for example, Tetrahedron Lett. 1997, 38, 3841).

The process (A) according to the invention can be carried out in two variants. It is possible either to initially charge a compound of the formula (II) or to initially charge a compound of the formula (III). Process (A) is to be considered a tandem reaction of the processes (B) and (C) described below.

The formula (II) provides a general definition of the $\Delta^1$-pyrrolines required as starting materials for carrying out the process (A). In this formula, $R^1$, $R^2$, $R^3$ and m preferably, particularly preferably and very particularly preferably have those meanings which have already been mentioned in connection with the description of the substances of the formula (I) according to the invention as being preferred, particularly preferred, etc. for these radicals. Z preferably represents bromine, iodine, —OSO$_2$CF$_3$ or —OSO$_2$(CF$_2$)$_3$CF$_3$, particularly preferably bromine, —OSO$_2$CF$_3$ or —OSO$_2$(CF$_2$)$_3$CF$_3$, very particularly preferably bromine or —OSO$_2$CF$_3$.

$\Delta^1$-Pyrrolines of the formula (II) can be prepared by known processes (cf. WO 98/22438). $\Delta^1$-Pyrrolines of the formula (II) can also be obtained by a process which is described below.

The formula (III) provides a general definition of the (hetero)cycles required as starting materials for carrying out the process (A) according to the invention. In this formula, $Y^1$ preferably represents O (oxygen). $X^1$ preferably represents O (oxygen) or NR$^8$. E preferably represents bromine, chlorine, iodine or —OSO$_2$CF$_3$, with particular preference bromine, chlorine or iodine, with very particular preference bromine or chlorine. A, R$^6$, R$^7$ and R$^8$ represent preferably, with particular preference or with very particular preference those definitions already stated as being preferred, particularly preferred, etc. for these radicals in connection with the description of the substances of the formula (I) according to the invention.

The (hetero)cycles of the formula (III) are known in some cases.

(Hetero)cycles of the Formula (III-a)

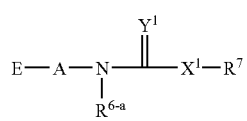

(III-a)

in which
E, A, Y$^1$, X$^1$ and R$^7$ have the meanings given above,
R$^{6-a}$ represents hydrogen, may be prepared, for example, by
a) reacting isocyanates of the formula (X)

 (X)

in which
E and A have the meanings given above,
with alcohols and/or amines of the formula (XI)

H—X$^1$—R$^7$ (XI)

in which
X$^1$ and R$^7$ have the meanings given above,
or with compounds of the formula (XII)

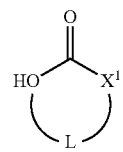

(XII)

in which
X has the meanings given above,
L represents alkylene optionally substituted one or more times by alkyl
optionally in the presence of a diluent (e.g. toluene, dioxane, dimethyl sulphoxide).

The formula (III-a) provides a general definition of the (hetero)cycles which can be prepared by process (a). In this formula, A and R$^7$ preferably, with particular preference or with very particular preference represent those definitions already stated as being preferred, particularly preferred, etc. for these radicals in connection with the description of the substances of the formula (I) according to the invention. E, $Y^1$ and $X^1$ represent preferably, with particular preference or with very particular preference those definitions already stated as being preferred, particularly preferred, etc. for these radicals in connection with the description of the substances of the formula (III) according to the invention. R$^{6-a}$ preferably represents hydrogen.

The formula (X) provides a general definition of the isocyanates required as starting materials for carrying out the process (a). In this formula, A represents preferably, with particular preference or with very particular preference those definitions already stated as being preferred, particularly preferred, etc., for these radicals in connection with the description of the substances of the formula (I) according to the invention. E represents preferably, with particular preference or with very particular preference those definitions already stated as being preferred, particularly preferred, etc. for these radicals in connection with the description of the substances of the formula (III) according to the invention.

Isocyanates of the formula (X) are known.

The formula (XI) provides a general definition of the alcohols and/or amines required as starting materials for carrying out the process (a). In this formula, R$^7$ represents preferably, with particular preference or with very particular preference those definitions already stated as being preferred, particularly preferred, etc. for these radicals in connection with the description of the substances of the formula (I) according to the invention. X$^1$ represents preferably, with particular preference or with very particular preference those definitions already stated as being preferred, particularly preferred, etc. for these radicals in connection with the description of the substances of the formula (III) according to the invention.

Alcohols and amines of the formula (XI) are known.

The formula (XII) provides a general definition of the compounds additionally required as starting materials for carrying out the process (a). In this formula, X$^1$ represents preferably, with particular preference or with very particular preference those definitions already stated as being preferred, particularly preferred, etc. for these radicals in connection with the description of the substances of the formula (III) according to the invention. L represents preferably $C_2$–$C_4$-alkylene optionally substituted from one to four times by $C_1$–$C_4$-alkyl, particularly preferably $C_2$–$C_3$-alkylene optionally substituted from one to three times by $C_1$–$C_4$-alkyl, with very particular preference methylene or ethylene each optionally substituted once or twice by identical or different methyl, ethyl, n-propyl or i-propyl substituents. Compounds of the formula (XII) are known.

(Hetero)cycles of the Formula (III-b)

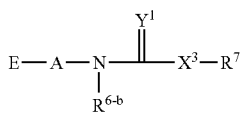

(III-b)

in which
E, A, $Y^1$ and $R^7$ have the meanings given above,
$X^3$ represents O (oxygen),
$R^{6-b}$ represents alkyl, may be prepared, for example, by
b) reacting amines of the formula (XIII)

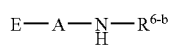

(XIII)

in which
E, A and $R^{6-b}$ have the meanings given above,
with a chloroformate of the formula (XIV)

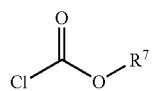

(XIV)

in which
$R^7$ has the meanings given above,
in the presence of N,O-bis(trimethylsilyl)acetamide and, where appropriate, in the presence of a diluent (e.g. dichloromethane) (cf. Syn. Commun. 1985, 15, 1025–1031).

The formula (III-b) provides a general definition of the (hetero)cycles which can be prepared by the process (b). In this formula, A represents preferably, with particular preference or with very particular preference those definitions already stated as being preferred, particularly preferred, etc. for these radicals in connection with the description of the substances of formula (I) according to the invention. E represents preferably, with particular preference or with very particular preference those definitions already stated as being preferred, particularly preferred, etc. for these radicals in connection with the description of the substances of formula (III) according to the invention. $R^{6-b}$ represents preferably $C_1$–$C_6$-alkyl, with particular preference $C_1$–$C_4$-alkyl, with very particular preference methyl, ethyl, n-propyl, i-propyl, n-butyl, i-butyl, s-butyl or t-butyl.

The formula (XIII) provides a general definition of the amines required as starting materials for carrying out the process (d). In this formula, E and A represent preferably, with particular preference or with very particular preference those definitions already stated as being preferred, particularly preferred, etc. for these radicals in connection with the description of the substances of formula (I) according to the invention. $R^{6-b}$ represents preferably $C_1$–$C_6$-alkyl, with particular preference $C_1$–$C_4$-alkyl, with very particular preference methyl, ethyl, n-propyl, i-propyl, n-butyl, i-butyl, s-butyl or t-butyl.

Amines of the formula (XIII) are known.

The formula (XIV) provides a general definition of the chloroformates required as starting materials for carrying out the process (b). In this formula, $R^7$ represents preferably, with particular preference or with very particular preference those definitions already stated as being preferred, particularly preferred, etc. for these radicals in connection with the description of the substances of formula (I) according to the invention.

Chloroformates of the formula (XIV) are known.

(Hetero)cycles of the formula (III-c)

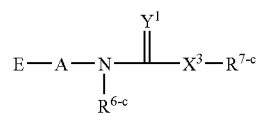

(III-c)

in which
E, A and $Y^1$ have the meanings given above,
$X^3$ represents O (oxygen),
$R^{6-c}$ and $R^{7-c}$ together represent alkylene optionally substituted one or more times by alkyl, may be prepared, for example, by
c) reacting isocyanates of the formula (X)

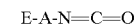

E-A-N=C=O   (X)

in which
E and A have the meanings given above,
with a dioxolane of the formula (XV)

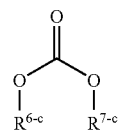

(XV)

in which
$R^{6-c}$ and $R^{7-c}$ have the meanings given above, where appropriate in the presence of an acid binder (e.g. caesium fluoride) and, where appropriate, in the presence of a diluent (e.g. dimethyl sulphoxide) (cf. JP 2000-290265).

The formula (III-c) provides a general definition of the (hetero)cycles which can be prepared by process (c). In this formula, A represents preferably, with particular preference or with very particular preference those definitions already stated as being preferred, particularly preferred, etc. for these radicals in connection with the description of the substances of formula (I) according to the invention. E represents preferably, with particular preference or with very particular preference those definitions already stated as being preferred, particularly preferred, etc. for these radicals in connection with the description of the substances of formula (III) according to the invention. $R^{6-c}$ and $R^{7-c}$ together represent preferably $C_2$–$C_4$-alkylene optionally substituted from one to four times by $C_1$–$C_4$-alkyl, with particular preference $C_2$–$C_3$-alkylene optionally substituted from one to three times by $C_1$–$C_4$-alkyl, with very particular preference methylene or ethylene substituted once or twice by methyl, ethyl, n-propyl or i-propyl.

The isocyanates of the formula (X) required as starting materials for carrying out the process (c) have already been described in connection with the elucidation of the process (a).

The formula (XV) provides a general definition of the dioxolanes required as starting materials for carrying out the process (c). In this formula, $R^{6-c}$ and $R^{7-c}$ preferably, with particular preference and with very particular preference represent those definitions already stated as being preferred, particularly preferred, for these radicals in connection with the description of the substances of formula (III-c).

Dioxolanes of the formula (XV) are known.

Suitable diboronic esters for carrying out process (A) according to the invention are 4,4',4',5,5,5',5'-octamethyl-2,2'-bis-1,3,2-dioxaborolane, 5,5,540 ,5'-tetramethyl-2,2'-bis-1,3,2-dioxaborinane, 4,4,4',4',6,6'-hexamethyl-2,2'-bis-1,3,2-dioxaborinane or 2,2'-bis-1,3,2-benzodioxaborole. Preference is given to using 4,4,4',4',5,5,5',5'-octamethyl-2,2'-bis-1,3,2-dioxaborolane, 5,5,5',5'-tetramethyl-2,2'-bis-1,3,2-dioxaborinane or 4,4,4',4',6,6'-hexamethyl-2,2'-bis-1,3,2-dioxaborinane, particularly preferably 4,4,4',4',5,5,5',5'-octamethyl-2,2'-bis-1,3,2-dioxaborolane or 5,5,5',5'-tetramethyl-2,2'-bis-1,3,2-dioxaborinane, very particularly preferably 4,4,4',4',5,5,5',5'-octamethyl-2,2'-bis-1,3,2-dioxaborolane.

When carrying out the process (A) according to the invention, in general 1 mol or a slight excess of a diboronic ester and 1 mol or a slight excess of a compound of the formula (III), and 3% of a palladium catalyst, are employed per mole of the compound of the formula (II). However, it is also possible to employ the reaction components in other ratios. It is possible to initially charge the compound of the formula (II) or, alternatively, the compound of the formula (III). Work-up is carried out by customary methods. In general, the reaction mixture is diluted with water and extracted with ethyl acetate. The organic phase is washed, dried, filtered and concentrated. The residue is, if appropriate, freed from any impurities that may still be present using customary methods, such as chromatography or recrystallization.

Process (B)

The formula (IV) provides a general definition of the $\Delta^1$-pyrrolines required as starting materials for carrying out the process (B) according to the invention. In this formula, $R^1$, $R^2$, $R^4$ and m preferably, particularly preferably and very particularly preferably have those meanings which have already been mentioned in connection with the description of the substances of the formula (I) according to the invention as being preferred, particularly preferred, etc. for these radicals. $Z^2$ preferably represents (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl, particularly preferably (4,4,5,5-tetramethyl-1,3,2-dioxaborolan)-2-yl, (5,5-dimethyl-1,3,2-dioxaborinan)-2-yl or (4,4,6-trimethyl-1,3,2-dioxaborinan)-2-yl, very particularly preferably (4,4,5,5-tetramethyl-1,3,2-dioxaborolan)-2-yl or (5,5-dimethyl-1,3,2-dioxaborinan)-2-yl.

$\Delta^1$-Pyrrolines of the formula (IV) can be prepared by d) reacting compounds of the formula (II)

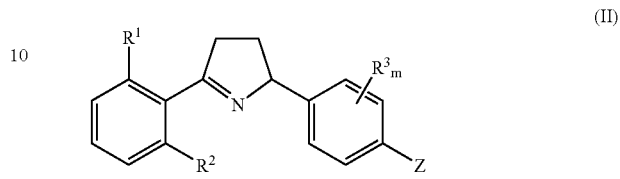

in which $R^1$, $R^2$, $R^4$, m and $Z^1$ have the meanings given above, with a diboronic ester in the presence of a catalyst, if appropriate in the presence of an acid binder and if appropriate in the presence of a diluent (cf. J. Org. Chem. 1995, 60, 7508; Tetrahedron Lett. 1997, 38, 3447).

Diboronic esters suitable for carrying out the process (d) have already been mentioned in the description of the process (A) according to the invention.

The heterocycles of the formula (III) required as starting materials for carrying out the process (B) according to the invention have already been described above in the description of process (A).

When carrying out the process (B) according to the invention, in general 1 mol or a slight excess of a compound of the formula (III) is employed per mole of the compound of the formula (V). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

Process (C)

The $\Delta^1$-pyrrolines of the formula (II) required as starting materials for carrying out the process (C) according to the invention have already been described in the description of process (A).

The formula (V) provides a general definition of the boronic acid derivatives required as starting materials for carrying out the process (C) according to the invention. In this formula, $Y^1$ represents preferably O (oxygen). $X^1$ represents preferably O (oxygen) or $NR^8$. $Z^2$ represents preferably (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl, particularly preferably (4,4,5,5-tetramethyl-1,3,2-dioxaborolan)-2-yl, (5,5-dimethyl-1,3,2-dioxaborinan)-2-yl or (4,4,6-trimethyl-1,3,2-dioxaborinan)-2-yl, very particularly preferably (4,4,5,5-tetramethyl-1,3,2-dioxaborolan)-2-yl or (5,5-dimethyl-1,3,2-dioxaborinan)-2-yl. A, $R^6$, $R^7$ and $R^8$ represent preferably, with particular preference or with very particular preference those definitions already stated as being preferred, particularly preferred, etc. for these radicals in connection with the description of the substances of the formula (I) according to the invention.

The compounds of the formula (V) are known or can be prepared by known processes.

When carrying out the process (C) according to the invention, in general 1 mol or a slight excess of a compound of the formula (V) is employed per mole of the compound of the formula (II). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

Process (D)

The formula (II-a) provides a general definition of the $\Delta^1$-pyrrolines required as starting materials for carrying out the process (D) according to the invention. In this formula, $R^1$, $R^2$, $R^4$ and m preferably, particularly preferably and very particularly preferably have those meanings which have already been mentioned in connection with the description of the substances of the formula (I) according to the invention as being preferred, particularly preferred, etc., for these radicals. $Z^3$ preferably represents bromine or iodine.

$\Delta^1$-Pyrrolines of the formula (II-a) can be prepared by known processes (cf. WO 98/22438).

The formula (VI) provides a general definition of the organometallic compounds required as starting materials for carrying out the process (D) according to the invention. In this formula, $Y^1$ represents preferably O (oxygen). $X^1$ represents preferably O (oxygen) or $NR^8$. M represents preferably ZnCl, Sn(Me)$_3$ or Sn(n-Bu)$_3$. A, $R^6$, $R^7$ and $R^8$ represents preferably, with particular preference or with very particular preference those definitions already stated as being preferred, particularly preferred, etc. for these radicals in connection with the description of the substances of formula (I) according to the invention.

Organometallic compounds of the formula (VI) are known in some cases or can be prepared by known methods. It is possible, for example, to prepare compounds of the formula (VI) in situ from the corresponding compounds of the formula (III) in which X represents —OSO$_2$CF$_3$ (cf. Tetrahedron Lett. 1995, 36, 9085).

When carrying out the process (D) according to the invention, in general 1 mol or a slight excess of a compound of the formula (VI) is employed per mole of the compound of the formula (II-a). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

Preparation of Starting Materials for Processes (A), (B), (C) and (D)

The $\Delta^1$-pyrrolines of the formulae (II), (IV) and (II-a) required as starting materials for carrying out the processes (A), (B), (C) and (D) according to the invention may also be prepared by e) reacting amides of the formula (XVI)

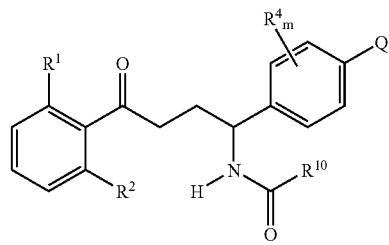

(XVI)

in which
Q represents $Z^1$, $Z^2$ or $Z^3$,
$R^{10}$ represents alkyl, haloalkyl, phenyl or benzyl,
$R^1$, $R^2$, $R^4$, m, $Z^1$, $Z^2$ and $Z^3$ have the meanings given above, with an N-deacylating agent in the presence of a diluent.

The formula (XVI) provides a general definition of the amides required as starting materials for carrying out the process (e). In this formula, $R^1$, $R^2$, $R^4$ and m represent preferably, with particular preference or with very particular preference those definitions already stated as being preferred, particularly preferred, etc. for these radicals in connection with the description of the substances of the formula (I) according to the invention. Q represents $Z^1$, $Z^2$ or $Z^3$ or represents the preferred, particularly preferred and very particularly preferred definitions of these radicals which have already been described above. $R^{10}$ represents preferably $C_1$–$C_4$-alkyl, $C_1$–$C_4$-haloalkyl, phenyl or benzyl, with particular preference methyl, ethyl, phenyl or benzyl, with very particular preference methyl, phenyl or benzyl.

The amides of the formula (XVI) required as starting materials for carrying out the process (e) may be prepared by f) reacting cyclopropanes of the formula (XVII)

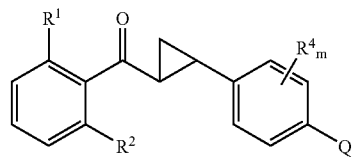

(XVII)

in which $R^1$, $R^2$, $R^4$, m and Q have the meanings given above,
with nitrites of the formula (XVIII)

$R^{10}$—CN (XVIII)

in which $R^{10}$ has the meanings given above
and a protic acid or trimethylsilyl tetrafluoroborate.

The formula (XVII) provides a general definition of the cyclopropanes required as starting materials for carrying out the process (f). In this formula, $R^1$, $R^2$, $R^4$ and m represent preferably, with particular preference or with very particular preference those definitions already stated as being preferred, particularly preferred or very particularly preferred for these radicals in connection with the description of the substances of the formula (I) according to the invention. Q represents $Z^1$, $Z^2$ or $Z^3$ or represents the preferred, particularly preferred and very particularly preferred definitions of these radicals which have already been described above.

The formula (XVIII) provides a general definition of the nitriles required as starting materials for carrying out the process (f). In this formula, $R^{10}$ represents preferably $C_1$–$C_4$-alkyl, $C_1$–$C_4$-haloalkyl, phenyl or benzyl, with particular preference methyl, ethyl, phenyl or benzyl, with very particular preference methyl, phenyl or benzyl.

Suitable protic acids when carrying out process (f) include all acids which can commonly be used for this purpose. A preferred possibility for use is sulphuric acid.

As trimethylsilyltetrafluoroborate for carrying out process (f), the compound of the formula (XIX)

is suitable. The reagent of the formula (XIX) is known (cf. Tetrahedron Lett. 1984, 25, 577–578).

The reaction temperatures for carrying out process (f) may be varied within a relatively wide range. It is normal to operate at temperatures between −20° C. and +60° C., preferably between −10° C. and 30° C.

The cyclopropanes of the formula (XVII) required as starting materials for carrying out the process (f) may be prepared by g) reacting chalcones of the formula (XX)

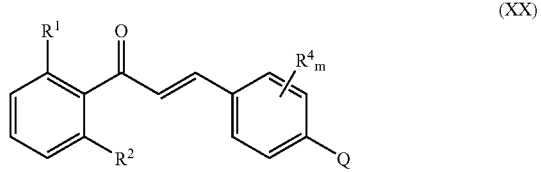

in which $R^1$, $R^2$, $R^4$, m and Q have the meanings given above, with a trialkylsulphoxonium ylide in the presence of a base and, where appropriate, in the presence of a diluent.

The formula (XX) provides a general definition of the chalcones required as starting materials when carrying out the process (g). In this formula, $R^1$, $R^2$, $R^4$ and m represent preferably, with particular preference or with very particular preference those definitions already stated as being preferred, particularly preferred or very particularly preferred for these radicals in connection with the description of the substances of the formula (I) according to the invention. Q represents $Z^1$, $Z^2$ or $Z^3$ or represents a preferred, particularly preferred and very particularly preferred definition of these radicals which have already been described above.

As a trialkylsulphoxonium ylide for carrying out the process (g) it is preferred to use trimethylsulphoxonium ylide.

As bases when carrying out process (g) it is possible to use alkali metal hydrides, alkoxides and hydroxides. Preference is given to using sodium hydride, potassium 2-methyl-2-propoxide, sodium methoxide or potassium hydroxide, with particular preference sodium hydride.

Suitable diluents when carrying out process (g) include dimethyl sulphoxide, tetrahydrofuran, acetonitrile, toluene or diethylene glycol, and mixtures thereof. It is preferred to use dimethyl sulphoxide (cf. Tetrahedron Asymmetry 1998, 9, 1035).

The reaction temperatures for carrying out process (g) according to the invention may be varied within a relatively wide range. It is normal to operate at temperatures between −20° C. and +120° C., preferably between 0° C. and 60° C., with particular preference between 20° C. and 40° C.

The chalcones of the formula (XX) required as starting materials for carrying out process (g) are known.

When carrying out process (e), the amides of the formula (XVI) are N-deacylated in the reaction to give pyrrolines of the formulae (II), (IV), and (II-a) using protic acids (cf. J. Org. Chem. 1978, 43, 4593), inorganic bases (cf. J. Chem. Soc. 1964, 4142), hydrazines (cf. J. Org. Chem. 1978, 43, 3711) or biotransformation with enzymes (cf. Appl. Microbiol. Biotechnol. 1997, 47, 650). Other customary methods of deacylating amides are described in T. W. Greene, P. G. M. Wuts, Protective Groups in Organic Synthesis (Ed. 3, New York, Wiley 1999, pp. 553–555).

As N-deacylating agents it is preferred to use protic acids or organic acids, with particular preference aqueous hydrochloric acid, aqueous hydrobromic acid or trifluoroacetic acid, with very particular preference aqueous hydrochloric acid; preferably inorganic bases, with particular preference barium hydroxide [Ba(OH)$_2$] and sodium hydroxide (NaOH) and preferably biotransformations, with particular preference using acylases.

In the case of N-deacylation by means of biotransformations, the compounds of the formulae (II), (IV), and (II-a) are obtained with one of the two enantiomers in excess.

Suitable diluents when carrying out process (e) include water or alcohols and mixtures of these. Preference is given to using water, methanol or ethanol or mixtures of two or three of these three diluents.

The reaction temperatures when carrying out process (e) may be varied within a relatively wide range. It is normal to operate at temperatures between 20° C. and 200° C., preferably between 60° C. and 140° C., with particular preference between 80° C. and 120° C. Where the N-deacylation is carried out enzymatically using acylases, it is normal to operate between 20° C. and 60° C., preferably between 20° C. and 40° C.

When carrying out process (e) it is normal to use 2 parts by volume of a protic acid per part by volume of a 10% strength (w/v) alcoholic solution of amide of the formula (XVI). However, other ratios of the reaction components may also be chosen. Work-up is carried out by customary methods. In general, the reaction mixture is neutralized with sodium hydroxide solution and then extracted with ethyl acetate and the organic phase is dried, filtered and concentrated.

Process (E)

The formula (VII) provides a general definition of the $\Delta^1$-pyrrolines required as starting materials when carrying out the process (E) according to the invention. In this formula, $R^1$, $R^2$, A, $R^4$ and m represent preferably, with particular preference or with very particular preference those definitions already stated as being preferred, particularly preferred, etc. for these radicals in connection with the description of the substances of formula (I) according to the invention.

Δ¹-Pyrrolines of the formula (VII) are novel. They may be prepared by h) reacting Δ¹-pyrrolines of the formula (I-b)

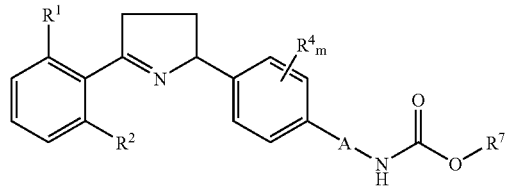
(I-b)

in which

R¹, R², A, R⁴, m and R⁷ have the meanings given above, with a mineral acid (e.g. hydrochloric acid, sulphuric acid) or a base (e.g. sodium hydroxide, potassium hydroxide) where appropriate in the presence of a diluent (e.g. alcohols such as methanol, ethanol or water or mixtures of these).

The Δ¹-pyrrolines of the formula (I-b) required as starting materials when carrying out the process (h) are a subgroup of the compounds of the formula (I) according to the invention. In the formula (I-b), R¹, R², A, R⁴, m and R⁷ represent preferably, with particular preference or with very particular preference those definitions already stated as being preferred, particularly preferred, etc. for these radicals in connection with the description of the substances of the formula (I) according to the invention. Δ¹-Pyrrolines of the formula (I-b) may be prepared by one of the processes (A), (B), (C) or (D) according to the invention.

The formula (VIII) provides a general definition of the iso(thio)cyanates required as starting materials when carrying out the process (E) of the invention. In this formula, Y and R⁷ represent preferably, with particular preference or with very particular preference those definitions already stated as being preferred, particularly preferred, etc. for these radicals in connection with the description of the substances of the formula (I) according to the invention.

Iso(thio)cyanates of the formula (VIII) are known and/or may be prepared by known processes.

The formula (IX) provides a general definition of the (thio)carbonates required as starting materials when carrying out the process (E) of the invention. In this formula, Y and R⁷ represent preferably, with particular preference or with very particular preference those definitions already stated as being preferred, particularly preferred, etc. for these radicals in connection with the description of the substances of the formula (I) according to the invention. X² represents preferably O (oxygen) or S (sulphur).

(Thio)carbonates of the formula (IX) are known and/or may be prepared by known processes.

When carrying out the process (E) according to the invention, in general 1 mol or a slight excess of a compound of the formula (VIII) and/or 1 mol or a slight excess of a compound of the formula (IX) are employed per mole of compound of the formula (VII). However, it is also possible to employ the reaction components in other proportions. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

Chiral Compounds of the Formula (I-a)

To prepare chiral compounds of the formula (I-a), it is possible, for example, to subject Δ¹-pyrrolines of the formula (II-b)

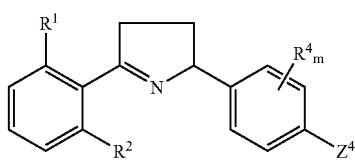
(II-b)

in which

R¹, R², R⁴ and m have the meanings given above,

Z⁴ represents chlorine, bromine or iodine to an optical resolution. To this end, for example, methods of preparative chromatography, preferably the high performance liquid chromatography (HPLC) method, are employed. Here, a chiral stationary silica gel phase is used. A tris(3,5-dimethylphenylcarbamate)-cellulose-modified silica gel has been found to be particularly suitable for separating the compounds of the formula (II-b) into the two enantiomers. This separating material is commercially available. However, it is also possible to use other stationary phases. Suitable mobile phases are all customary inert organic solvents, and mixtures of these. Preference is given to using optionally halogenated aliphatic, alicyclic or aromatic hydrocarbons, such as petroleum ether, hexane, heptane, cyclohexane; dichloromethane, chloroform; alcohols, such as methanol, ethanol, propanol; nitriles, such as acetonitrile; esters, such as methyl acetate or ethyl acetate. Particular preference is given to using aliphatic hydrocarbons, such as hexane or heptane, and alcohols, such as methanol or propanol, very particularly preferably n-heptane and isopropanol or mixtures of these. In general, the separation is carried out at temperatures between 10° C. and 60° C., preferably between 10° C. and 40° C., particularly preferably at room temperature. The (R)-configured enantiomers obtained in this manner are then used as starting materials for the processes (A), (C) or (D).

When carrying out the processes (A), (B), (C) and (D) according to the invention, in each case a palladium catalyst is employed, which for its part can be used with or without addition of further ligands. The catalyst used is preferably PdCl₂(dppf) [dppf=1,1'-bis(diphenylphosphino)ferrocene], Pd(PPh₃)₄, PdCl₂(PPh₃)₂, PdCl₂(CH₃CN)₂, Pd₂(dba)₃ [dba=dibenzylideneacetone] or Pd(OAc)₂, particularly preferably PdCl₂(dppf), Pd(PPh₃)₄, PdCl₂(PPh₃)₂ or Pd(OAc)₂, very particularly preferably PdCl₂(dppf) or PdCl₂(PPh₃)₂.

Suitable ligands are triarylphosphines, trialkylphosphines or arsines. Preference is given to using dppf, PPh₃, P(t-Bu)₃, Pcy₃ or AsPh₃, particularly preferably dppf.

Suitable diluents for carrying out the processes (A), (B) and (C) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane. Particular preference is given to using acetone, dimethoxyethane, dioxane, tetrahydrofuran, dimethylformamide, dimethylacetamide, dimethyl sulphoxide, ethanol, toluene or, if appropriate, mixtures of the diluents mentioned with water.

Suitable diluents for carrying out the processes (D) and (E) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichlorethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole. Particular preference when carrying out process (D) according to the invention is given to using dioxane, tetrahydrofuran or toluene.

Suitable acid binders for carrying out the processes (A), (B), (C) and (D) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, alkali metal fluorides, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to operate without additional acid binder, or to employ an excess of the amine component, so that it simultaneously acts as acid binder. Barium hydroxide, sodium hydroxide, potassium hydroxide, tripotassium phosphate, caesium carbonate, potassium carbonate, sodium carbonate, potassium acetate, triethylamine, potassium tert-butoxide, caesium fluoride or potassium fluoride are used with particular preference.

Suitable acid binders for carrying out the process (E) according to the invention are in each case all inorganic and organic bases which are customary for such reactions. Preference is given to using alkali metal carbonates, such as sodium carbonate, potassium carbonate, potassium bicarbonate, sodium bicarbonate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to operate without additional acid binder.

When carrying out the processes (A), (B) and (C) according to the invention, the reaction temperatures can in each case be varied within a relatively wide range. In general, the reactions are carried out at temperatures between 0° C. and 140° C., preferably between 20° C. and 120° C., particularly preferably between 60° C. and 100° C.

When carrying out the process (D) according to the invention, the reaction temperatures can in each case be varied within a relatively wide range. In general, the reaction is carried out at temperatures between 0° C. and 140° C., preferably between 20° C. and 120° C.

When carrying out the process (E) according to the invention, the reaction temperatures can in each case be varied within a relatively wide range. In general, the reaction is carried out at temperatures between 0° C. and 100° C., preferably between 20° C. and 50° C.

All processes according to the invention are generally carried out under atmospheric pressure. However, in each case it is also possible to operate under elevated or reduced pressure.

The active compounds according to the invention are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria inigratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

In particular, the compounds of the formula (I) according to the invention have excellent activity against caterpillars, beetle larvae, spider mites, aphids and leaf-mining flies.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds according to the invention can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds according to the invention with extenders, that is liquid solvents and/or solid carriers, optionally with the use of surfactants, that is emulsifiers and/or dispersants and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks;

suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates;

suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used in customary commercial form or in their formulations as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly advantageous co-components are, for example, the following:

Fungicides:
aldimorph, ampropylfos, ampropylfos-potassium, andoprim, anilazine, azaconazole, azoxystrobin,
benalaxyl, benodanil, benomyl, benzamacril, benzamacryl-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irunamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G, OK-8705, OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucpyranosyl]-amino]-4-methoxy-1H-pyrrolo[2,3-d]pyrimidine-5-carbonitrile,
2-aminobutane,
2-bromo-2-(bromomethyl)-pentanedinitrile, 2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4,5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl]-phenyl-2-methylpropyl]-2,6-dimethylmorpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran-3'-one Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, *Entomopfthora* spp., eprinomectin, esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses,
lambda-cyhalothrin, lufenuron,
malathion, mecarbam, metaldehyde, methamidophos, *Metharhizium anisopliae, Metarhizium flavoviride*, methidathion, methiocarb, methomyl, methoxyfenozide, metolcarb, metoxadiazone, mevinphos, milbemectin, monocrotophos,
naled, nitenpyram, nithiazine, novaluron,
omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, selamectin, silafluofen, spinosad, sulphotep, sulprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii*,
YI 5302,
zeta-cypermethrin, zolaprofos,
(1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate.
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl]-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitro-guanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds according to the invention, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The preferred transgenic plants or plant cultivars (i.e. those obtained by genetic engineering) which are to be treated according to the invention include all plants which, in the genetic modification, received genetic material which imparted particular advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® ((tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still to be developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

They have, for example, excellent activity against the development stages of ticks such as, for example, *Amblyomma hebraeum*, against parasitic flies such as, for example, *Lucilia cuprina* and against fleas such as, for example, *Ctenocephalides felis*.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) according to the invention can be used as formulations (for example powders, emulsions, free-flowing compositions), which comprise the active compounds according to the invention in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden window frames and doors, plywood, chipboard, joinery or wooden products which are used quite generally in housebuilding or in building joinery.

The active compounds according to the invention can be used as such, in the form of concentrates or in generally customary formulations, such as powders, granules, solutions, suspensions, emulsions or pastes.

The formulations mentioned can be prepared in a manner known per se, for example by mixing the active compounds according to the invention with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably a-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxy-conazole, hexaconazole, azaconazole, propiconazole, tebuconazole, cyproconazole, metconazole, imazalil, dichlorfluanid, tolylfluanid, 3-iodo-2-propinyl-butyl carbamate, N-octylisothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile *Oligochaeta*, such as *Serpulidae*, and by shells and species from the *Ledamorpha* group (goose barnacles), such as various *Lepas* and *Scalpellum* species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile *Entomostraka* groups, which come under the generic term *Cirripedia* (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butyl-carbamate, tolylfluanid and azoles such as azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetra-methylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all development stages. These pests include:
From the order of the Scorpionidea, for example, *Buthus occitanus*.
From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus* and *Dermatophagoides forinae*.
From the order of the Araneae, for example, *Aviculariidae* and *Araneidae*.

From the order of the Opiliones, for example, *Pseudoscorpiones chelifer*, *Pseudoscorpiones cheiridium* and *Opiliones phalangium*.

From the order of the Isopoda, for example, *Oniscus asellus* and *Porcellio scaber*.

From the order of the Diplopoda, for example, *Blaniulus guttulatus* and *Polydesmus* spp.

From the order of the Chilopoda, for example, *Geophilus* spp.

From the order of the Zygentoma, for example, *Ctenolepisma* spp., *Lepisma saccharina* and *Lepismodes inquilinus*.

From the order of the Blattaria, for example, *Blatta orientalies*, *Blattella germanica*, *Blattella asahinai*, *Leucophaea maderae*, *Panchlora* spp., *Parcoblatta* spp., *Periplaneta australasiae*, *Periplaneta americana*, *Periplaneta brunnea*, *Periplaneta fuliginosa* and *Supella longipalpa*.

From the order of the Saltatoria, for example, *Acheta domesticus*.

From the order of the Dermaptera, for example, *Forficula auricularia*.

From the order of the Isoptera, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., *Latheticus oryzae*, *Necrobia* spp., *Ptinus* spp., *Rhizopertha dominica*, *Sitophilus granarius*, *Sitophilus oryzae*, *Sitophilus zeamais* and *Stegobium paniceum*.

From the order of the Diptera, for example, *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga camaria*, *Simulium* spp., *Stomoxys calcitrans* and *Tipula paludosa*.

From the order of the Lepidoptera, for example, *Achroia grisella*, *Galleria mellonella*, *Plodia interpunctella*, *Tinea cloacella*, *Tinea pellionella* and *Tineola bisselliella*.

From the order of the Siphonaptera, for example, *Ctenocephalides canis*, *Ctenocephalides felis*, *Pulex irritans*, *Tunga penetrans* and *Xenopsylla cheopis*.

From the order of the Hymenoptera, for example, *Camponotus herculeanus*, *Lasius fuliginosus*, *Lasius niger*, *Lasius umbratus*, *Monomorium pharaonis*, *Paravespula* spp. and *Tetramorium caespitum*.

From the order of the Anoplura, for example, *Pediculus humanus capitis*, *Pediculus humanus corporis* and *Phthirus pubis*.

From the order of the Heteroptera, for example, *Cimex hemipterus*, *Cimex lectularius*, *Rhodinus prolixus* and *Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, unpressurized spray products, for example pump and atomizer sprays, automatic misting systems, foggers, foams, gels, evaporator products with evaporator tablets made of cellulose or polymer, liquid evaporators, gel and membrane evaporators, propeller-driven evaporators, energy-free, or passive evaporation systems, moth papers, moth bags and moth gels, as granules or dusts, in baits for spreading or in bait stations.

The preparation and use of the substances according to the invention is shown in the examples below.

PREPARATION EXAMPLES

Example 1

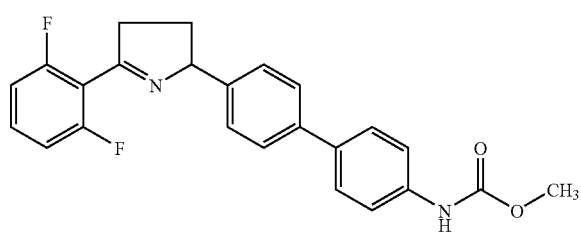

5-(2,6-Difluorophenyl)-2-[4-(4,4,5,5-tetramethyl-1,3,2-dioxaborolan-2-yl)phenyl]-3,4-dihydro-2H-pyrrole (0.96 g, 2.50 mmol) is dissolved in 10 ml of N,N-dimethylacetamide. Methyl 4-bromophenylcarbamate (III-1) (0.69 g, 3.00 mmol), PdCl$_2$[dppf] (0.05 g, 0.07 mmol) and 3.75 ml of sodium carbonate solution (2 M) are added in succession and the mixture is subsequently stirred at 80° C. for 16 h. It is cooled to room temperature and extracted with water/ethyl acetate and the organic phase is separated off, dried over magnesium sulphate, filtered and concentrated under reduced pressure. The crude product is purified by silica gel chromatography (cyclohexane/ethyl acetate 91:9→80:20, each v/v).

This gives 0.35 g (32% of theory) of methyl 4'-[5-(2,6-difluorophenyl)-3,4-dihydro-2H-pyrrol-2-yl]-1,1'-biphenyl-4-ylcarbamate.

HPLC: log P (pH 2.3)=2.31 (purity: 93%)

log P (pH 7.5)=3.52

Example 2

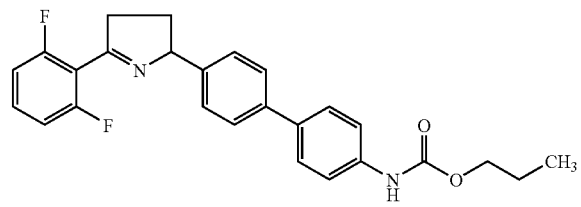

5-(2,6-Difluorophenyl)-2-[4-(4,4,5,5-tetramethyl-1,3,2-dioxaborolan-2-yl)phenyl]-3,4-dihydro-2H-pyrrole (0.96 g, 2.50 mmol) and n-propyl 4-bromophenylcarbamate (III-2) (0.77 g, 3.00 mmol) are dissolved in 10 ml of 1,2-dimethoxyethane. PdCl$_2$[dppf] (0.05 g, 0.07 mmol) and 3.75 ml of sodium carbonate solution (2 M) are added in succession and the mixture is subsequently stirred at 80° C. for 16 h. It is cooled to room temperature and extracted with water/ethyl acetate and the organic phase is separated off, dried over magnesium sulphate, filtered and concentrated under reduced pressure. The crude product is purified by silica gel chromatography (cyclohexane/ethyl acetate 20:1→6:1→2:1, each v/v).

This gives 0.28 g (25% of theory) of n-propyl 4'-[5-(2,6-difluorophenyl)-3,4-dihydro-2H-pyrrol-2-yl]-1,1'-biphenyl-4-ylcarbamate.

HPLC: log P (pH 2.3)=3.02 (purity: 98%)
log P (pH 7.5)=4.24

Example 3

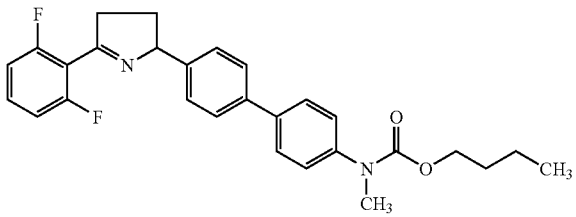

5-(2,6-Difluorophenyl)-2-[4-(4,4,5,5-tetramethyl-1,3,2-dioxaborolan-2-yl)phenyl]-3,4-dihydro-2H-pyrrole (0.96 g, 2.50 mmol) is dissolved in 20 ml of N,N-dimethylacetamide. n-Butyl 4-bromophenyl(methyl)carbamate (III-3) (0.86 g, 3.00 mmol), PdCl$_2$[dppf] (0.05 g, 0.07 mmol) and 3.75 ml of sodium carbonate solution (2 M) are added in succession and the mixture is subsequently stirred at 90° C. for 16 h. It is cooled to room temperature and the reaction mixture is concentrated under reduced pressure. The residue is taken up in ethyl acetate and washed with water. The organic phase is separated off, dried over magnesium sulphate, filtered and concentrated under reduced pressure. The crude product is purified by silica gel chromatography (cyclohexane/ethyl acetate 10:1→6:1, each v/v).

This gives 0.48 g (41% of theory) of n-butyl 4'-[5-(2,6-difluorophenyl)-3,4-dihydro-2H-pyrrol-2-yl]-1,1'-biphenyl-4-yl(methyl)carbamate.

HPLC: log P (pH 2.3)=3.76 (purity: 98%)
log P (pH 7.5)=4.92

Example 4

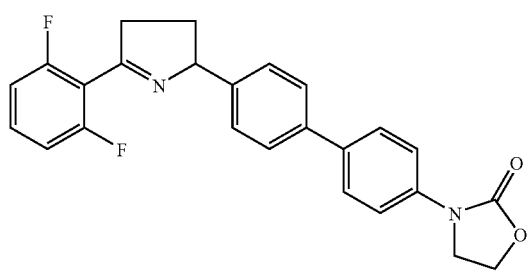

5-(2,6-Difluorophenyl)-2-[4-(4,4,5,5-tetramethyl-1,3,2-dioxaborolan-2-yl)phenyl]-3,4-dihydro-2H-pyrrole (0.96 g, 2.50 mmol) is dissolved in 20 ml of N,N-dimethylacetamide. 3-(4-Bromophenyl)-1,3-oxazolidin-2-one (III-4) (0.73 g, 3.00 mmol), PdCl$_2$[dppf] (0.05 g, 0.07 mmol) and 3.75 ml of sodium carbonate solution (2 M) are added in succession and the mixture is subsequently stirred at 90° C. for 16 h. It is cooled to room temperature, water is added, and the precipitate is filtered off with suction. The crude product is purified by silica gel chromatography (cyclohexane/acetone 20:1→10:1, each v/v).

This gives 0.75 g (66% of theory) of 3-{4'-[5-(2,6-difluorophenyl)-3,4-dihydro-2H-pyrrol-2-yl]-1,1'-biphenyl-4-yl}-1,3-oxazolidin-2-one.

HPLC: log P (pH 2.3)=2.13 (purity: 92%)
log P (pH 7.5)=3.28

Example 5

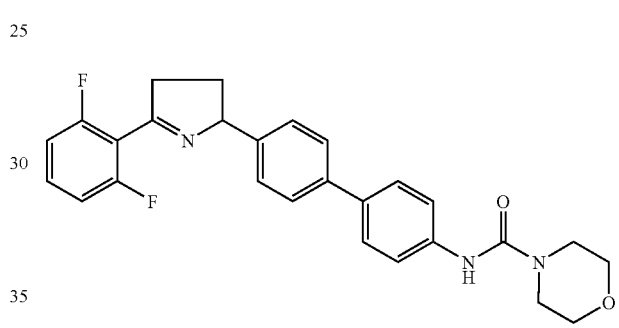

5-(2,6-Difluorophenyl)-2-[4-(4,4,5,5-tetramethyl-1,3,2-dioxaborolan-2-yl)phenyl]-3,4-dihydro-2H-pyrrole (0.96 g, 2.50 mmol) and N-(4-bromophenyl)-4-morpholine-carboxamide (III-5) (0.86 g, 3.00 mmol) are dissolved in 10 ml of 1,2-dimethoxyethane. PdCl$_2$[dppf] (0.05 g, 0.07 mmol) and 3.75 ml of sodium carbonate solution (2 M) are added in succession and the mixture is subsequently stirred at 80° C. for 16 h. It is cooled to room temperature and extracted with water/ethyl acetate and the organic phase is separated off, dried over magnesium sulphate, filtered and concentrated under reduced pressure. The crude product is purified by silica gel chromatography (cyclohexane/ethyl acetate 2:1→1:1, each v/v).

This gives 0.35 g (30% of theory) of N-{4'-[5-(2,6-difluorophenyl)-3,4-dihydro-2H-pyrrol-2-yl]-1,1'-biphenyl-4-yl}-4-morpholinecarboxamide.

HPLC: log P (pH 2.3)=1.87 (purity: 100%)

log P (pH 7.5)=2.96

In analogy to Examples 1 to 5 above and in accordance with the general preparation details, the compounds of the formula (I) indicated in the following table are obtained.

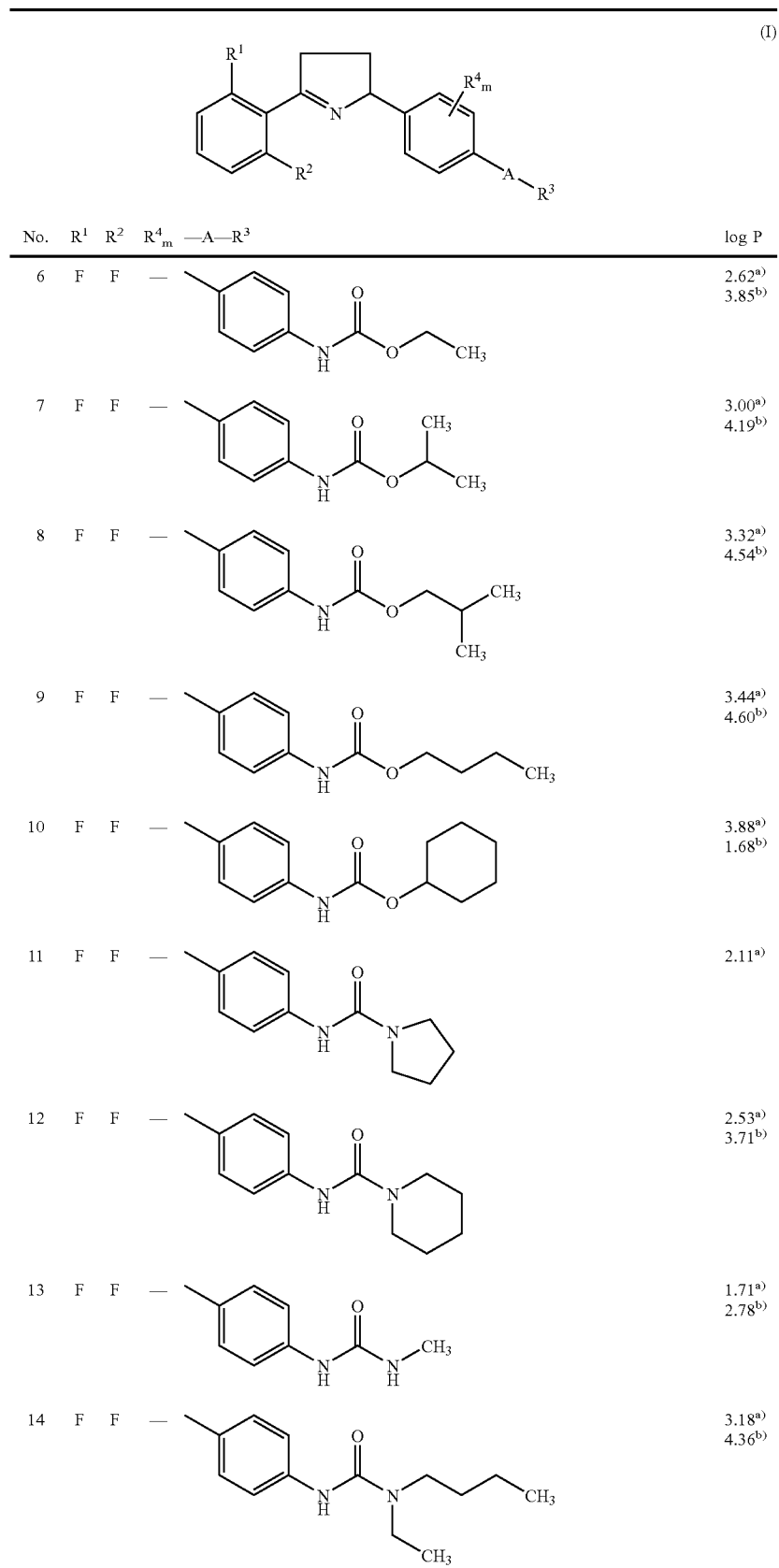

-continued
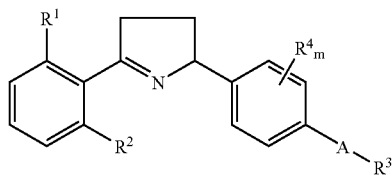
(I)
| No. | R¹ | R² | R⁴ₘ | —A—R³ | log P |
|---|---|---|---|---|---|
| 15 | F | F | — | 4-NHC(O)NH-butyl-phenyl | 2.48[a]<br>3.47[b] |
| 16 | F | F | — | 4-NHC(O)O-CH(CH₃)CH(CH₃)₂-phenyl | 3.82[a]<br>4.77[b] |
| 17 | F | F | — | 4-NHC(O)O-CH(CH₃)CH₂CH₃-phenyl | 4.82[b] |
| 18 | F | F | — | 4-NHC(O)O-pentyl-phenyl | 3.87[a]<br>4.89[b] |
| 19 | F | F | — | 4-NHC(O)O-hexyl-phenyl | 4.46[a]<br>5.26[b] |
| 20 | F | F | — | 4-NHC(O)O-CH(CH₃)-phenyl-phenyl | 3.63[a] |
| 21 | F | F | — | 4-NHC(O)O-CH₂CH₂CH(CH₃)₂-phenyl | 3.72[a] |
| 22 | F | F | — | 5-NHC(O)NH-phenyl-pyridin-2-yl | 2.71[a]<br>3.98[b] |
| 23 | F | F | — | 4-NHC(O)O-CH₂C(CH₃)₃-phenyl | 3.76[a] |

-continued
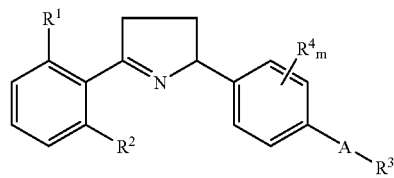
(I)
| No. | R¹ | R² | R⁴ₘ | —A—R³ | log P |
|---|---|---|---|---|---|
| 24 | F | F | — | 4-NHC(O)O-CH(CH₂CH₃)₂ phenyl | 3.76[a] |
| 25 | F | F | — | 4-NHC(O)O-CH₂CH₂-phenyl | 3.62[a]<br>4.64[b] |
| 26 | F | F | — | 4-NHC(O)O-CH₂-(2-furyl) | 3.01[a]<br>4.10[b] |
| 27 | F | F | — | 4-NHC(O)O-CH₂-(2-thienyl) | 3.28[a]<br>4.36[b] |
| 28 | F | F | — | 4-NHC(O)O-CH₂CH₂-O-CH₂-CH(C₂H₅)(C₄H₉) | 5.13[a]<br>5.97[b] |
| 29 | F | F | — | 4-NHC(O)O-CH₂CH₂-N(C₃H₇)₂ | 1.74[a]<br>5.52[b] |
| 30 | F | F | — | 4-NHC(O)O-CH₂CH₂-N(CH₃)₂ | 1.37[a] |
| 31 | F | F | — | 4-NHC(O)O-CH₂CH₂-OCH₃ | 2.24[a]<br>3.45[b] |
| 32 | F | F | — | 4-NHC(O)O-CH₂CH₂-OC₂H₅ | 2.52[a]<br>3.75[b] |

-continued
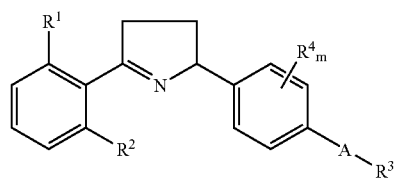
(I)
| No. | R¹ | R² | R⁴ₘ | —A—R³ | log P |
|---|---|---|---|---|---|
| 33 | F | F | — | 4-position: -NH-C(=O)-O-CH₂-CH₂-O-CH₂-CH₂-CH₂-CF₂-CF₃ | 3.82[a] |
| 34 | F | F | — | 4-position: -NH-C(=O)-O-(CH₂-CH₂-O)₂-CH₂-CH₂-CH₂-CF₂-CF₃ | 3.70[a] 4.73[b] |
| 35 | F | F | — | 4-position: -N(CH₃)-C(=O)-O-CH₃ | 2.58[a] 3.79[b] |
| 36 | F | F | — | 4-position: -N(CH₃)-C(=O)-O-CH₂-CH₂-CH₃ | 3.32[a] 4.52[b] |
| 37 | F | F | — | 4-position: -N(CH₃)-C(=O)-O-CH₂-CH₃ | 2.92[a] 4.16[b] |
| 38 | F | F | — | 4-position: 5-methyl-2-oxo-oxazolidin-3-yl | 2.40[a] |
| 39 | F | F | — | 4-position: -N(CH₃)-C(=O)-O-CH₂-C(CH₃)₃ | 4.11[a] 5.19[b] |
| 40 | F | F | — | 4-position: -N(CH₃)-C(=O)-O-CH(CH₃)₂ | 3.30[a] 4.50[b] |

-continued (I)

| No. | R¹ | R² | R⁴ₘ | —A—R³ | log P |
|-----|----|----|-----|-------|-------|
| 41 | F | F | — | ![structure with N(CH3)C(O)OCH2CH(CH3)2 on tolyl] | 3.79[a)]<br>4.89[b)] |
| 42 | F | F | — | ![pyridyl-NHC(O)O-benzyl structure] | 2.54[a)]<br>3.88[b)] |

Preparation of Starting Materials of the Formula (III)

Example (III-1)

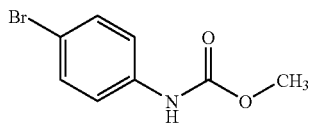
(III-1)

A solution of 4-bromophenyl isocyanate (3.26 g, 16.46 mmol) in 15 ml of toluene is added dropwise at room temperature to 1 ml of methanol and 20 ml of toluene and the mixture is stirred at room temperature for a further 16 hours. The reaction mixture is concentrated under reduced pressure. The crude product is purified by silica gel chromatography (cyclohexane/ethyl acetate 2:1, v/v).

This gives 3.65 g (88% of theory) of methyl 4-bromophenylcarbamate.

HPLC: log P (pH 2.3)=2.27 (purity: 92%)

Example (III-2)

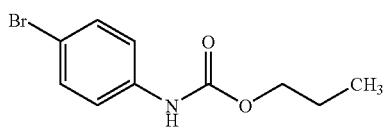
(III-2)

1.85 ml of n-propanol is introduced in 10 ml of toluene under an argon atmosphere. 4-Bromophenyl isocyanate (3.26 g, 16.46 mmol) is added in portions at room temperature and the reaction mixture is stirred at room temperature for a further 16 hours. The reaction mixture is concentrated under reduced pressure. The crude product is purified by silica gel chromatography (cyclohexane/ethyl acetate 2:1, v/v).

This gives 4.13 g (95% of theory) of n-propyl 4-bromophenylcarbamate.

HPLC: log P (pH 2.3)=3.12 (purity: 98%)

Example (III-3)

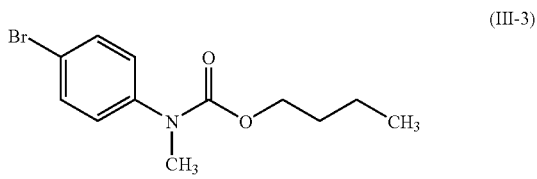
(III-3)

N-(4-Bromophenyl)-N-methylamine (1.50 g, 8.06 mmol) is introduced in 15 ml of dichloromethane under an argon atmosphere and then N,O-bis(trimethylsilyl)-acetamide (1.97 g, 9.67 mmol) is added and the mixture is stirred at room temperature for 1 hour. It is then cooled to 0° C. and butyl chloroformate (1.23 ml, 9.67 mmol) is added dropwise. The mixture is warmed to room temperature and stirred at this temperature for a further 16 hours. It is cooled again to 0° C., quenched with potassium dihydrogen phosphate/disodium hydrogen phosphate buffer pH 7 and extracted with dichloromethane and the organic phase is separated off, washed with saturated sodium chloride solution, dried over magnesium sulphate, filtered and concentrated under reduced pressure.

This gives 1.13 g (98% of theory) of n-butyl-4-bromophenyl(methyl)carbamate.

HPLC: log P (pH 2.3) 3.88 (purity: 96%)

Example (III-4)

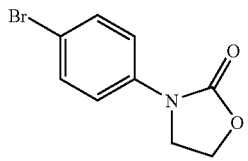

(III-4)

4-Bromophenyl isocyanate (2.00 g, 10.10 mmol) is introduced in 15 ml of dimethyl sulphoxide under an argon atmosphere and then dioxolan-2-one (0.89 g, 10.10 mmol) and caesium fluoride (0.15 g, 1.01 mmol) are added, whereupon a white precipitate is formed. The mixture is stirred at 140° C. under argon for 2 hours. The reaction mixture is cooled and poured into ice-water and the precipitate formed is filtered off with suction, dried and recrystallized from isopropanol.

This gives 1.55 g (61% of theory) of 3-(4-bromophenyl)-1,3-oxazolidin-2-one.

HPLC: log P (pH 2.3)=2.02 (purity: 96%)

Example (III-5)

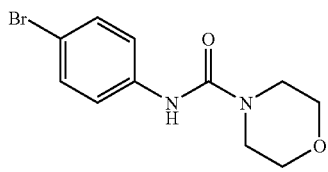

(III-5)

1.96 ml of morpholine is introduced in 15 ml of dioxane under an argon atmosphere. At room temperature, 4-bromophenyl isocyanate (2.97 g, 15.00 mmol) is added in portions and the reaction mixture is stirred at room temperature for a further 16 hours. The crude product is subsequently filtered off with suction and isolated by silica gel chromatography (cyclohexane/ethyl acetate 2:1, v/v).

This gives 3.13 g (66% of theory) of N-(4-bromophenyl)-4-morpholinecarboxamide.

HPLC: log P (pH 2.3)=1.75 (purity: 91%)

Preparation of Starting Materials of the Formula (VII)

Example (VII-1)

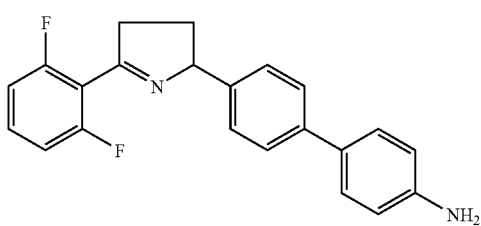

(VII-1)

Methyl 4'-[5-(2,6-difluorophenyl)-3,4-dihydro-2H-pyrrol-2-yl]-1,1'-biphenyl-4-yl-carbamate (Example 1) (0.23 g, 0.53 mmol) is dissolved in 2 ml of ethanol. Following addition of potassium hydroxide (0.03 g, 0.53 mmol) the mixture is stirred under reflux for 16 hours. The precipitate is filtered off with suction and the crude product is purified by silica gel chromatography (cyclohexane/ethyl acetate 2:1, v/v).

This gives 0.13 g (69% of theory) of 4'-[5-(2,6-difluorophenyl)-3,4-dihydro-2H-pyrrol-2-yl]-1'-biphenyl-4-amine.

HPLC: log P (pH 2.3)=1.25 (purity: 97%)

The logP values stated in the above tables and Preparation Examples are determined in accordance with EEC Directive 79/831 Annex V.A8 by HPLC (High Performance Liquid Chromatography) using a reversed-phase column (C 18). Temperature: 43° C.

In the acidic range at pH 2.3 the determination takes place using 0.1% aqueous phosphoric acid and acetonitrile as the mobile phases; linear gradient from 10% acetonitrile to 90% acetonitrile. Corresponding results are marked in the tables by "a)"

In the neutral range at pH 7.5 the determination takes place using 0.01 molar aqueous phosphate buffer solution and acetonitrile as the mobile phases; linear gradient from 10% acetonitrile to 90% acetonitrile. Corresponding results are marked in the tables by "b)"

Calibration is carried out using unbranched alkan-2-ones (having 3 to 16 carbon atoms), with known logP values (the logP values determined on the basis of the retention times using linear interpolation between two successive alkanones).

Use Examples

Example A

*Heliothis virescens* Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Soya bean shoots (*Glycine max*) are treated by being dipped into the preparation of active compound of the desired concentration and are populated with *Heliothis virescens* caterpillars whilst the leaves are still moist.

After the desired period of time, the kill in % is determined. 100% means that all caterpillars have been killed; 0% means that none of the caterpillars has been killed.

In this test, at an active compound concentration of 100 ppm, for example, the compounds 2 and 6–8 from the Preparation Examples exhibit a good activity of at least 95%. The test results can be seen in detail from Table A below.

TABLE A

Plant-damaging insects
*Heliothis virescens* test

| Active compounds | | Active compound concentration in ppm | Kill rate in % after 7$^d$ |
|---|---|---|---|
| [Structure: 2,6-difluorophenyl-dihydropyrrole-biphenyl-NHC(O)O-CH2CH3] | (6) | 100 | 100 |
| [Structure: 2,6-difluorophenyl-dihydropyrrole-biphenyl-NHC(O)O-CH2CH2CH3] | (2) | 100 | 100 |
| [Structure: 2,6-difluorophenyl-dihydropyrrole-biphenyl-NHC(O)O-CH(CH3)2] | (7) | 100 | 100 |
| [Structure: 2,6-difluorophenyl-dihydropyrrole-biphenyl-NHC(O)O-CH2CH(CH3)2] | (8) | 100 | 100 |

Example B

*Phaedon larvae* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) whilst the leaves are still moist.

After the desired period of time, the kill in % is determined. 100% means that all beetle larvae have been killed; 0% means that none of the beetle larvae has been killed.

In this test, at an active compound concentration of 100 ppm, for example, the compounds 1, 2, 6, 7, 16, 18–21, 24, 25, 27, 29, 32, 35, 37 from the Preparation Examples exhibit a good activity of at least 85%. The test results can be seen in detail from Table B below.

TABLE B plant-damaging insects
*Phaedon* larvae test

| Active compounds | | Active compound concentration in ppm | Kill rate in % after 7$^d$ |
|---|---|---|---|
| [2,6-difluorophenyl-pyrroline-biphenyl-NH-C(O)O-CH₃] | (1) | 100 | 100 |
| [2,6-difluorophenyl-pyrroline-biphenyl-NH-C(O)O-CH₂CH₃] | (6) | 100 | 100 |
| [2,6-difluorophenyl-pyrroline-biphenyl-NH-C(O)O-CH₂CH₂CH₃] | (2) | 100 | 100 |
| [2,6-difluorophenyl-pyrroline-biphenyl-NH-C(O)O-CH(CH₃)₂] | (7) | 100 | 100 |
| [2,6-difluorophenyl-pyrroline-biphenyl-NH-C(O)O-CH₂CH₂CH₂CH₃] | (9) | 100 | 100 |
| [2,6-difluorophenyl-pyrroline-biphenyl-NH-C(O)O-cyclohexyl] | (10) | 100 | 100 |

TABLE B-continued plant-damaging insects
*Phaedon* larvae test

| Active compounds | | Active compound concentration in ppm | Kill rate in % after 7$^d$ |
|---|---|---|---|
| [structure: 2,6-difluorophenyl-pyrroline-biphenyl-NH-C(O)-pyrrolidine] | (11) | 100 | 100 |
| [structure: 2,6-difluorophenyl-pyrroline-biphenyl-NH-C(O)-piperidine] | (12) | 100 | 100 |
| [structure: 2,6-difluorophenyl-pyrroline-biphenyl-NH-C(O)-O-CH(CH$_3$)CH(CH$_3$)$_2$] | (16) | 100 | 100 |
| [structure: 2,6-difluorophenyl-pyrroline-biphenyl-NH-C(O)-O-pentyl] | (18) | 100 | 100 |
| [structure: 2,6-difluorophenyl-pyrroline-biphenyl-NH-C(O)-O-hexyl] | (19) | 100 | 100 |

TABLE B-continued
plant-damaging insects
*Phaedon* larvae test
| Active compounds | | Active compound concentration in ppm | Kill rate in % after 7[d] |
|---|---|---|---|
| 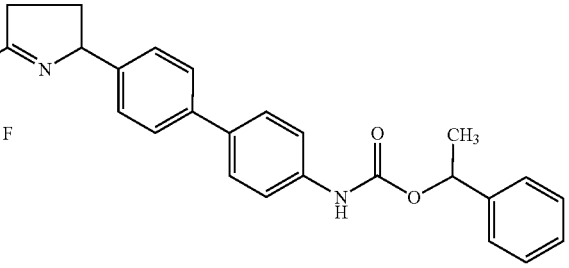 | (20) | 100 | 100 |
| 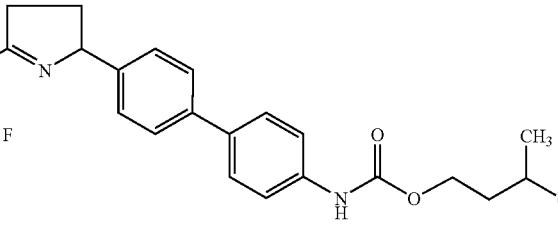 | (21) | 100 | 100 |
| 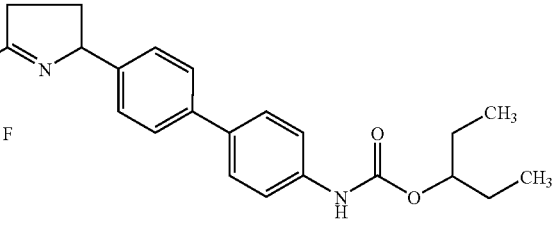 | (24) | 100 | 100 |
| 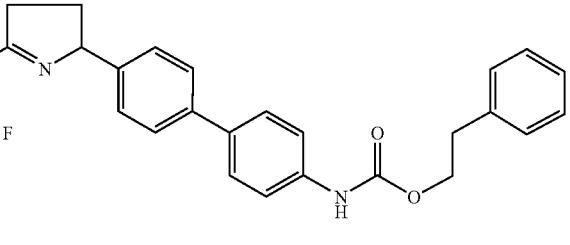 | (25) | 100 | 100 |
| 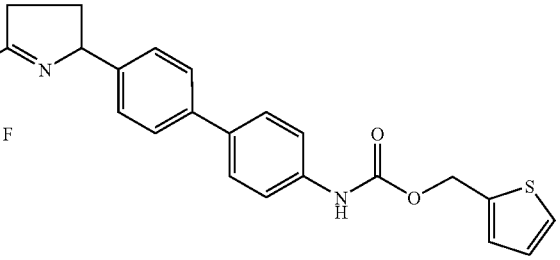 | (27) | 100 | 100 |

TABLE B-continued
plant-damaging insects
*Phaedon* larvae test
| Active compounds | | Active compound concentration in ppm | Kill rate in % after 7$^d$ |
|---|---|---|---|
| 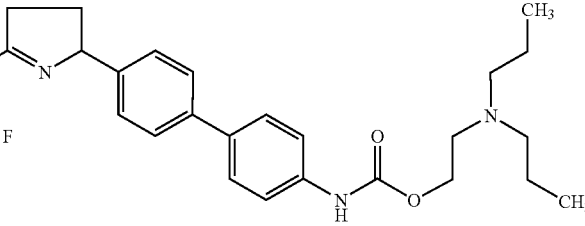 | (29) | 100 | 100 |
| 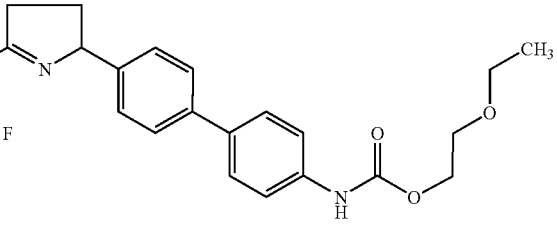 | (32) | 100 | 100 |
| 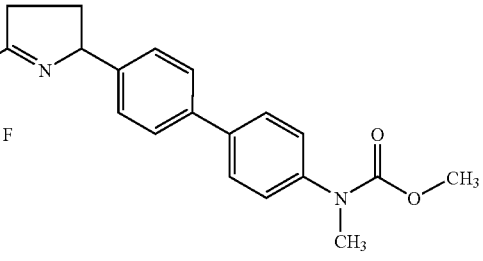 | (35) | 100 | 100 |
| 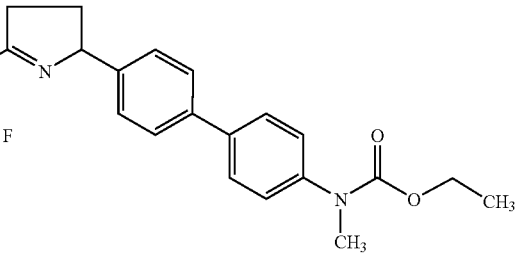 | (37) | 100 | 90 |

Example C

*Plutella* Test, Sensitive Strain

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the cabbage moth (*Plutella xylostella*, sensitive strain) whilst the leaves are still moist.

After the desired period of time, the kill in % is determined. 100% means that all caterpillars have been killed; 0% means that none of the caterpillars has been killed.

In this test, at an active compound concentration of 100 ppm, for example, the compounds 2, 6–8 and 23 from the Preparation Examples exhibit a good activity of at least 95%. The test results can be seen in detail from Table C below.

TABLE C plant-damaging insects
*Plutella* test, sensitive strain

| Active compounds | | Active compound concentration in ppm | Kill rate in % after $7^d$ |
|---|---|---|---|
| [structure] | (6) | 100 | 100 |
| [structure] | (2) | 100 | 100 |
| [structure] | (7) | 100 | 100 |
| [structure] | (8) | 100 | 100 |

TABLE C-continued plant-damaging insects
Plutella test, sensitive strain

| Active compounds | | Active compound concentration in ppm | Kill rate in % after 7$^d$ |
|---|---|---|---|
| [structure] | (23) | 100 | 100 |

Example D

Plutella Test, Resistant Strain

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the cabbage moth (*Plutella xylostella*, sensitive strain) whilst the leaves are still moist.

After the desired period of time, the kill in % is determined. 100% means that all caterpillars have been killed; 0% means that none of the beetle larvae has been killed.

In this test, at an active compound concentration of 100 ppm, for example, the compounds 2, 6–8 and 23 from the Preparation Examples exhibit a good activity of at least 95%. The test results can be seen in detail from Table D below.

TABLE D plant-damaging insects
Plutella test, resistant strain

| Active compounds | | Active compound concentration in ppm | Kill rate in % after 7$^d$ |
|---|---|---|---|
| [structure] | (6) | 100 | 100 |
| [structure] | (2) | 100 | 100 |

TABLE D-continued plant-damaging insects
*Plutella* test, resistant strain

| Active compounds | | Active compound concentration in ppm | Kill rate in % after 7$^d$ |
|---|---|---|---|
| [Structure with 2,6-difluorophenyl-pyrroline-biphenyl-NHC(O)O-isopropyl] | (7) | 100 | 100 |
| [Structure with 2,6-difluorophenyl-pyrroline-biphenyl-NHC(O)O-isobutyl] | (8) | 100 | 100 |
| [Structure with 2,6-difluorophenyl-pyrroline-biphenyl-NHC(O)O-neopentyl] | (23) | 100 | 100 |

Example E

*Spodoptera exigua* Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with army worm (*Spodoptera exigua*) caterpillars whilst the leaves are still moist.

After the desired period of time, the kill in % is determined. 100% means that all caterpillars have been killed; 0% means that none of the caterpillars has been killed.

In this test, at an active compound concentration of 100 ppm, for example, the compounds 2, 6–8 and 23 from the Preparation Examples exhibit a good activity of at least 95%. The test results can be seen in detail from Table E below.

TABLE E plant-damaging insects
*Spodoptera exigua* test

| Active compounds | | Active compound concentration in ppm | Kill rate in % after 7$^d$ |
|---|---|---|---|
| [structure with ethyl carbamate] | (6) | 100 | 100 |
| [structure with propyl carbamate] | (2) | 100 | 100 |
| [structure with isopropyl carbamate] | (7) | 100 | 100 |
| [structure with isobutyl carbamate] | (8) | 100 | 100 |
| [structure with neopentyl carbamate] | (23) | 100 | 100 |

Example F

*Spodoptera frugiperda* Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with army worm (*Spodoptera frugiperda*) caterpillars whilst the leaves are still moist.

After the desired period of time, the kill in % is determined. 100% means that all caterpillars have been killed; 0% means that none of the caterpillars has been killed.

In this test, at an active compound concentration of 100 ppm, for example, the compounds 1, 2, 4–7, 9, 10, 12, 14, 17, 18, 20–23, 25–28, 30, 31, 33, 34 and 37 from the Preparation Examples exhibit a good activity of at least 95%. The test results can be seen in detail from Table F below.

TABLE F plant-damaging insects
*Spodoptera frugiperda*-Test

| Active compounds | | Active compound concentration in ppm | Kill rate in % after 7$^d$ |
|---|---|---|---|
| [structure with F, F, pyrroline, biphenyl, NHC(O)OCH$_3$] | (1) | 100 | 100 |
| [structure with F, F, pyrroline, biphenyl, NHC(O)OCH$_2$CH$_3$] | (6) | 100 | 100 |
| [structure with F, F, pyrroline, biphenyl, NHC(O)OCH$_2$CH$_2$CH$_3$] | (2) | 100 | 100 |
| [structure with F, F, pyrroline, biphenyl, NHC(O)OCH(CH$_3$)$_2$] | (7) | 100 | 100 |
| [structure with F, F, pyrroline, biphenyl, NHC(O)OCH$_2$CH$_2$CH$_2$CH$_3$] | (9) | 100 | 100 |

TABLE F-continued plant-damaging insects
*Spodoptera frugiperda*-Test

| Active compounds | | Active compound concentration in ppm | Kill rate in % after 7$^d$ |
|---|---|---|---|
| [structure] | (5) | 100 | 100 |
| [structure] | (10) | 100 | 100 |
| [structure] | (12) | 100 | 100 |
| [structure] | (14) | 100 | 100 |
| [structure] | (18) | 100 | 100 |

TABLE F-continued plant-damaging insects
*Spodoptera frugiperda*-Test

| Active compounds | | Active compound concentration in ppm | Kill rate in % after $7^d$ |
|---|---|---|---|
| [structure] | (20) | 100 | 100 |
| [structure] | (21) | 100 | 100 |
| [structure] | (22) | 100 | 100 |
| [structure] | (23) | 100 | 100 |
| [structure] | (25) | 100 | 100 |

TABLE F-continued plant-damaging insects
*Spodoptera frugiperda*-Test

| Active compounds | | Active compound concentration in ppm | Kill rate in % after 7$^d$ |
|---|---|---|---|
| [structure] | (26) | 100 | 100 |
| [structure] | (27) | 100 | 100 |
| [structure] | (28) | 100 | 100 |
| [structure] | (30) | 100 | 100 |
| [structure] | (31) | 100 | 100 |

TABLE F-continued plant-damaging insects
*Spodoptera frugiperda*-Test

| Active compounds | | Active compound concentration in ppm | Kill rate in % after 7$^d$ |
|---|---|---|---|
| [structure with CF$_3$/CF$_2$ chain] | (33) | 100 | 100 |
| [structure with F$_3$C-CF$_2$ chain and diether] | (34) | 100 | 100 |
| [structure with N(CH$_3$)-C(O)-O-CH$_3$ carbamate] | (37) | 100 | 100 |
| [structure with oxazolidinone] | (4) | 100 | 100 |

Example G

*Tetranychus* Test (OP Resistant/Dip Treatment)

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites have been killed.

In this test, at an active compound concentration of 100 ppm, for example, the compounds 1, 2, 4, 6, 7, 17, 19, 22–24, 26–30 und 32–35 from the Preparation Examples exhibit a good activity of at least 85%. The test results can be seen in detail from Table G below.

TABLE G
plant-damaging insects
*Tetranychus* test (OP-resistant/dip treatment)
| Active compounds | | Active compound concentration in ppm | Kill rate in % after 7$^d$ |
|---|---|---|---|
| 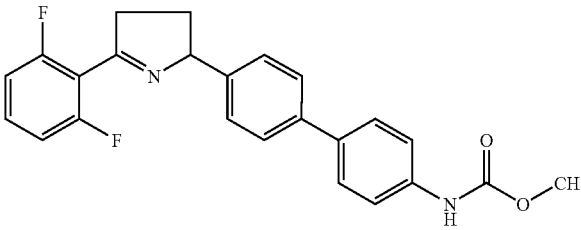 | (1) | 100 | 98 |
| 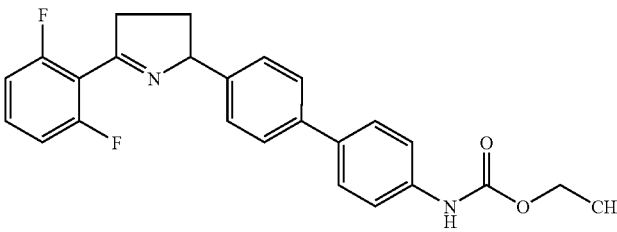 | (6) | 100 | 98 |
| 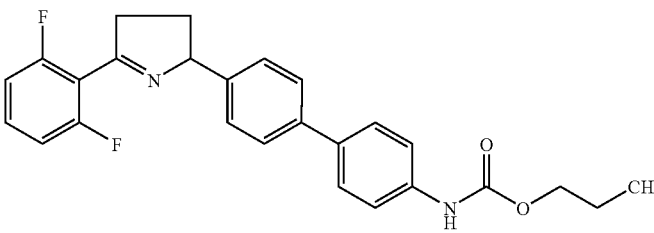 | (2) | 100 | 98 |
| 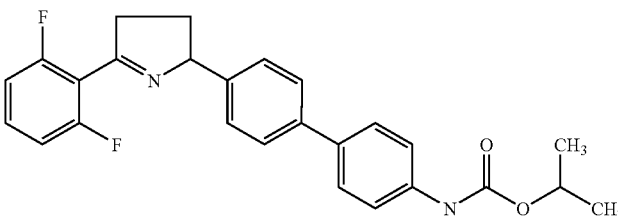 | (7) | 100 | 98 |
| 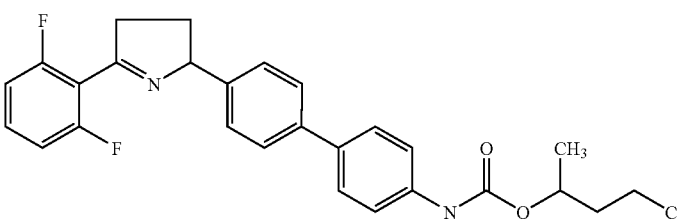 | (17) | 100 | 90 |
| 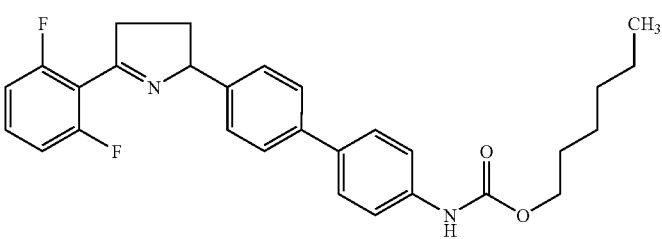 | (19) | 100 | 90 |

TABLE G-continued plant-damaging insects
Tetranychus test (OP-resistant/dip treatment)

| Active compounds | | Active compound concentration in ppm | Kill rate in % after 7$^d$ |
|---|---|---|---|
| [structure] | (22) | 100 | 90 |
| [structure] | (23) | 100 | 95 |
| [structure] | (24) | 100 | 95 |
| [structure] | (26) | 100 | 98 |
| [structure] | (27) | 100 | 98 |

TABLE G-continued plant-damaging insects
*Tetranychus* test (OP-resistant/dip treatment)

| Active compounds | | Active compound concentration in ppm | Kill rate in % after 7$^d$ |
|---|---|---|---|
| (structure) | (28) | 100 | 95 |
| (structure) | (29) | 100 | 98 |
| (structure) | (30) | 100 | 95 |
| (structure) | (32) | 100 | 98 |
| (structure) | (33) | 100 | 100 |

TABLE G-continued plant-damaging insects
Tetranychus test (OP-resistant/dip treatment)

| Active compounds | | Active compound concentration in ppm | Kill rate in % after 7$^d$ |
|---|---|---|---|
| [structure] | (34) | 100 | 90 |
| [structure] | (35) | 100 | 98 |
| [structure] | (4) | 100 | 90 |

Example H

*Diabrotica balteata* Test (Larvae in Soil)

Critical Concentration Test/Soil Insects—Treatment of Transgenic Plants

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually immaterial; only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the corresponding test insects are placed into the treated soil. After a further 7 days, the efficacy of the active compound is determined by counting the number of maize plants that have emerged (1 plant=20% activity).

Example J

*Heliothis virescens* Test (Treatment of Transgenic Plants)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trade mark of Monsanto Comp. USA) are treated by being dipped into the preparation of active compound of the desired concentration and populated with the tobacco budworm caterpillar *Heliothis virescens* whilst the leaves are still moist.

After the desired period of time, the kill in % is determined. 100% means that all caterpillars have been killed; 0% means that none of the caterpillars has been killed.

Example K

Test with *Boophilus microplus* Resistant/SP-Resistant Parkhurst Strain

Test animals: Adult satiated females

Solvent: Dimethyl sulphoxide 20 mg of active compound are dissolved in 1 ml of dimethyl sulphoxide. Lower concentrations are prepared by dilution in the same solvent.

The test is carried out in 5 replications. 1 μl of the solutions is injected into the abdomen, and the animals are transferred to dishes and kept in a climate-controlled room. After 7 days, activity is checked by examination for deposition of fertile eggs. Eggs whose fertility is not externally visible are stored in glass tubes in a controlled-environment cabinet until the larvae have hatched. An activity of 100% denotes that none of the ticks has laid fertile eggs.

In this test, for example, the following compounds from the Preparation Examples exhibit very good activity:

Example L

Test with Flies (*Musca domestica*)

Test animals: Adult *Musca domestica*, Reichswald strain (OP, SP, carbamate-resistant)

Solvent: Dimethyl sulphoxide 20 mg of active compound are dissolved in 1 ml dimethyl sulphoxide. Lower concentrations are prepared by dilution with distilled water.

2 ml of this active compound preparation are pipetted on filter paper discs (Ø9.5 cm) in Petri dishes of corresponding dimensions. After the filter discs have been dried, 25 test animals are transferred to the Petri dishes, which are then covered.

After 1, 3, 5, 24 and 48 hours the activity of the active compound preparation is measured. 100% means that all flies have been killed, 0% means that no fly has been killed.

In this test, for example, the following compound from the Preparation Examples exhibits very good activity:

TABLE K

Test with *Boophilus microplus* resistant/SP-resistant Parkhurst strain

| Active compounds | | Concentration in μg/animal | Activity/kill in % |
|---|---|---|---|
| 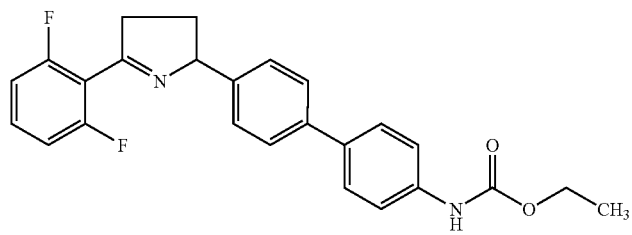 | (6) | 100/20 | 20/20 |
| 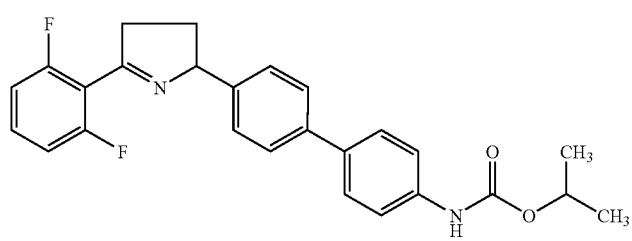 | (7) | 100/20 | 40/0 |
| 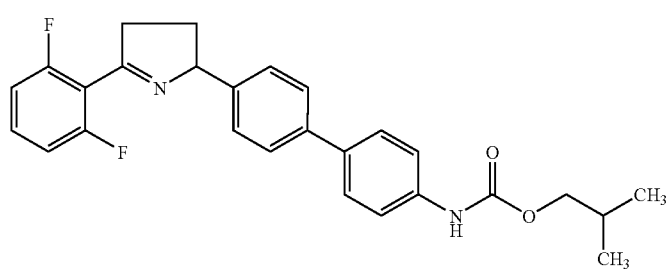 | (8) | 100/20/4 | 80/40/0 |

TABLE L

Test mit Fliegen (*Musca domestica*)

| Active compound | Concentration in ppm | Activity/ kill in % |
|---|---|---|
| 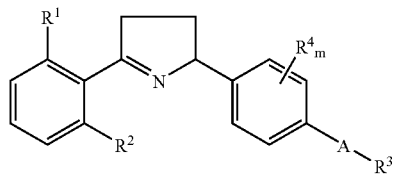 (13) | 100/20 | 30/0 |

What is claimed is:

1. A Δ$^1$-pyrroline of formula (I)

(I)

in which
R$^1$ represents halogen or methyl,
R$^2$ represents hydrogen or halogen,
R$^3$ represents —N(R$^6$)—C(=Y)—X—R$^7$,
A represents arylene that is optionally substituted from one to four times by identical or different substituents R$^5$,
Y represents O or S,
X represents O, S, or NR$^8$,
R$^4$ and R$^5$ independently of one another represent halogen, alkyl, alkoxy, alkylthio, haloalkyl, haloalkoxy, or haloalkylthio,
m represents 0, 1, 2, 3, or 4,
R$^6$ represents hydrogen or alkyl,
R$^7$ and R$^8$ independently of one another represent hydrogen; represent alkyl or alkenyl, each of which is optionally substituted one or more times by identical or different substituents selected from the group consisting of halogen, alkylcarbonyl, alkylcarbonyloxy, alkylamino, dialkylamino, alkoxy, alkylthio, alkoxyalkoxy, haloalkoxy, haloalkylthio, and halogenalkoxyalkoxy; or represent cycloalkyl, cycloalkylalkyl, aryl, arylalkyl, or saturated or unsaturated 5- to 10-membered heterocyclyl or heterocyclylalkyl, each of which is optionally substituted one or more times by identical or different substitutents selected from the group consisting of halogen, alkyl, haloalkyl, alkoxy, haloalkoxy, alkylthio, haloalkylthio, alkylcarbonyl, and alkoxycarbonyl, or
R$^6$ and R$^7$ together represent alkylene optionally substituted one or more times by alkyl, or
R$^7$ and R$^8$, together with the nitrogen atom to which they are attached, represent a saturated or unsaturated 5- to 10-membered heterocycle that optionally contains a further heteroatom group selected from the series —O—, —S—, and —NR$^9$— and that is optionally substituted one or more times by identical or different substituents selected from the group consisting of halogen, alkyl, alkoxy, alkylthio, haloalkyl, haloalkoxy, and haloalkylthio, and
R$^9$ represents hydrogen, alkyl, or alkenyl.

2. A Δ$^1$-pyrroline of formula (I) according to claim 1 in which
R$^1$ represents fluorine, chlorine, bromine, or methyl,
R$^2$ represents hydrogen, fluorine, chlorine, or bromine,
R$^3$ represents —N(R$^6$)—C(=Y)—X—R$^7$,
A represents arylene that is optionally substituted from one to three times by identical or different substituents R$^5$,
Y represents O or S,
X represents O, S, or NR$^8$,
R$^4$ and R$^5$ independently of one another represent fluorine, chlorine, bromine, $C_1$–$C_6$-alkyl, $C_1$–$C_6$-alkoxy, $C_1$–$C_6$-alkylthio, $C_1$–$C_6$-haloalkyl, $C_1$–$C_6$-haloalkoxy, or $C_1$–$C_6$-haloalkylthio,
m represents 0, 1, 2, or 3,
R$^6$ represents hydrogen or $C_1$–$C_6$-alkyl,
R$^7$ and R$^8$ independently of one another represent hydrogen; represent $C_1$–$C_{20}$-alkyl or $C_2$–$C_{20}$-alkenyl, each of which is optionally substituted one or more times by identical or different substituents selected from the group consisting of fluorine, chlorine, bromine, $C_1$–$C_6$-alkylcarbonyl, $C_1$–$C_6$-alkylcarbonyloxy, $C_1$–$C_6$-alkylamino, di-($C_1$–$C_6$-alkyl)amino, $C_1$–$C_{10}$-alkoxy, $C_1$–$C_{10}$-alkylthio, $C_1$–$C_{10}$-alkoxy-$C_1$–$C_{10}$-alkoxy, $C_1$–$C_{10}$-haloalkoxy, $C_1$–$C_{10}$-haloalkylthio, and $C_1$–$C_{10}$-haloalkoxy-$C_1$–$C_{10}$-alkoxy; or represent $C_3$–$C_{12}$-cycloalkyl, $C_3$–$C_7$-cycloalkyl-$C_1$–$C_4$-alkyl, aryl, aryl-$C_1$–$C_4$-alkyl, saturated or unsaturated 5- to 10-membered heterocyclyl or heterocyclyl-$C_1$–$C_4$-alkyl having 1 to 4 heteroatoms, containing 0 to 4 nitrogen atoms, 0 to 2 non-adjacent oxygen atoms, and/or 0 to 2 non-adjacent sulphur atoms, each of which is optionally substituted from one to four times by identical or different substituents selected from the group consisting of fluorine, chlorine, bromine, $C_1$–$C_6$-alkyl, $C_1$–$C_6$-alkoxy, $C_1$–$C_6$-alkylthio, $C_1$–$C_6$-haloalkyl, $C_1$–$C_6$-haloalkoxy, $C_1$–$C_6$-haloalkylthio, $C_1$–$C_6$-alkylcarbonyl, and $C_1$–$C_6$-alkoxycarbonyl, or
R$^6$ and R$^7$ together represent $C_2$–$C_4$-alkylene optionally substituted from one to four times by $C_1$–$C_4$-alkyl, or
R$^7$ and R$^8$, together with the nitrogen atom to which they are attached, represent a saturated or unsaturated 5- to 10-membered heterocycle that optionally contains a further heteroatom group selected from the series —O—, —S—, or —NR$^9$— and that is optionally substituted from one to four times by identical or different substituents selected from the group consisting of fluorine, chlorine, bromine, $C_1$–$C_6$-alkyl, $C_1$–$C_6$-alkoxy, $C_1$–$C_6$-alkylthio, $C_1$–$C_6$-haloalkyl, $C_1$–$C_6$-haloalkoxy, and $C_1$–$C_6$-haloalkylthio, and $R^9$ represents hydrogen, $C_1$–$C_6$-alkyl or $C_2$–$C_6$-alkenyl.

3. A $\Delta^1$-pyrroline of formula (I) according to claim 2 in which

A represents phenylene,

Y represents O or S, and

X represents O, S, or $NR^8$.

4. A $\Delta^1$-pyrroline of formula (I) according to claim 2 in which $R^7$ and $R^8$ independently of one another represent tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally substituted from one to four times by identical or different substituents selected from the group consisting of fluorine, chlorine, bromine, $C_1$–$C_6$-alkyl, $C_1$–$C_6$-alkoxy, $C_1$–$C_6$-alkylthio, $C_1$–$C_6$-haloalkyl, $C_1$–$C_6$-haloalkoxy, $C_1$–$C_6$-haloalkylthio, $C_1$–$C_6$-alkylcarbonyl, and $C_1$–$C_6$-alkoxycarbonyl.

5. A $\Delta^1$-pyrroline of formula (I) according to claim 1 in which $R^1$ represents fluorine, chlorine, or methyl, $R^2$ represents hydrogen, fluorine, or chlorine, $R^3$ represents —N($R^6$)—C(=Y)—X—$R^7$, A represents phenylene that is optionally substituted once or twice by identical or different substituents $R^5$, Y represents O or S, X represents O, S, or $NR^8$, $R^4$ and $R^5$ independently of one another represent fluorine, chlorine, $C_1$–$C_4$-alkyl, $C_1$–$C_4$-alkoxy, or $C_1$–$C_4$-alkylthio; or $C_1$–$C_4$-haloalkyl, $C_1$–$C_4$-haloalkoxy, or $C_1$–$C_4$-haloalkylthio having in each case 1 to 9 fluorine, chlorine, and/or bromine atoms, m represents 0, 1, or 2, $R^6$ represents hydrogen or $C_1$–$C_4$-alkyl, $R^7$ and $R^8$ independently of one another represent hydrogen; represent $C_1$–$C_{16}$-alkyl or $C_2$–$C_{16}$-alkenyl, each of which is optionally substituted one or more times by identical or different substituents selected from the group consisting of fluorine, chlorine, bromine, $C_1$–$C_4$-alkylcarbonyl, $C_1$–$C_4$-alkylcarbonyloxy, $C_1$–$C_4$-alkylamino, di-($C_1$–$C_4$-alkyl)amino, $C_1$–$C_{10}$-alkoxy, $C_1$–$C_{10}$-alkylthio, $C_1$–$C_{10}$-alkoxy-$C_1$–$C_6$-alkoxy, $C_1$–$C_{10}$-haloalkoxy, $C_1$–$C_{10}$-haloalkylthio, and $C_1$–$C_{10}$-haloalkoxy-$C_1$–$C_6$-alkoxy having in each case 1 to 21 fluorine, chlorine, and/or bromine atoms; or represent $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally substituted from one to three times by identical or different substituents selected from the group consisting of fluorine, chlorine, bromine, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio having in each case 1 to 9 fluorine, chlorine, and/or bromine atoms, $C_1$–$C_4$-alkylcarbonyl, and $C_1$–$C_4$-alkoxycarbonyl, or $R^6$ and $R^7$ together represent $C_2$–$C_3$-alkylene optionally substituted from one to three times by $C_1$–$C_4$-alkyl, or $R^7$ and $R^8$, together with the nitrogen atom to which they are attached, represent a saturated or unsaturated 5- to 7-membered heterocycle that optionally contains a further heteroatom group selected from the series —O—, —S—, and —$NR^9$— and that is optionally substituted from one to four times by identical or different substituents selected from the group consisting of fluorine, chlorine, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, and $C_1$–$C_4$-haloalkylthio having in each case 1 to 9 fluorine, chlorine, and/or bromine atoms, and $R^9$ represents hydrogen, $C_1$–$C_4$-alkyl or $C_2$–$C_4$-alkenyl.

6. A $\Delta^1$-pyrroline of formula (I) according to claim 5 in which $R^7$ and $R^8$, together with the nitrogen atom to which they are attached, represent piperidino, morpholino, thiomorpholino, piperazino, pyrrolidino, oxazolidino, thiazolidino, 4H-1-oxazinyl, or 4H-1-thiazinyl, each of which is optionally substituted from one to four times by identical or different substituents selected from the group consisting of fluorine, chlorine, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, and $C_1$–$C_4$-haloalkylthio having in each case 1 to 9 fluorine, chlorine, and/or bromine atoms.

7. A $\Delta^1$-pyrroline of formula (I) according to claim 1 in which $R^1$ represents fluorine or chlorine, $R^2$ represents hydrogen or fluorine, $R^3$ represents —N($R^6$)—C(=Y)—X—$R^7$, A represents 1,2-phenylene or 1,4-phenylene, each of which is optionally substituted once by $R^5$, Y represents O or S, X represents O, S, or $NR^8$, $R^4$ and $R^5$ independently of one another represent fluorine, chlorine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, methylthio, ethylthio, n-propylthio, i-propylthio, n-butylthio, i-butylthio, s-butylthio, t-butylthio, trifluoromethyl, trifluoroethyl, trifluoromethoxy, trifluoroethoxy, trifluoro-methylthio, or trifluoroethylthio, m represents 0 or 1, $R^6$ represents hydrogen, methyl, ethyl, n-propyl, i-propyl, n-butyl, i-butyl, s-butyl, or t-butyl, $R^7$ and $R^8$ independently of one another represent hydrogen; represent $C_1$–$C_{10}$-alkyl or $C_2$–$C_{10}$-alkenyl, each of which is optionally substituted one or more times by identical or different substituents selected from the group consisting of fluorine, chlorine, bromine, $C_1$–$C_4$-alkylcarbonyl, $C_1$–$C_4$-alkylcarbonyloxy, $C_1$–$C_4$-alkylamino, di-($C_1$–$C_4$-alkyl)amino, $C_1$–$C_{10}$-alkoxy, $C_1$–$C_8$-alkoxy-$C_1$–$C_6$-alkoxy, $C_1$–$C_{10}$-alkylthio, $C_1$–$C_{10}$-haloalkoxy, $C_1$–$C_{10}$-haloalkylthio having in each case 1 to 21 fluorine, chlorine, and/or bromine atoms, and $C_1$–$C_8$-haloalkoxy-$C_1$–$C_6$-alkoxy having 1 to 17 fluorine, chlorine, and/or bromine atoms; or represent $C_3$–$C_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl, or isoquinolinyl, each of which is optionally substituted from one to three times by identical or different substituents selected from the group consisting of fluorine, chlorine, bromine, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio having in each case 1 to 9 fluorine, chlorine, and/or bromine atoms, $C_1$–$C_4$-alkylcarbonyl, and $C_1$–$C_4$-alkoxycarbonyl, or $R^6$ and $R^7$ together represent methylene or ethylene, each of which is optionally substituted once or twice by identical or different methyl, ethyl, n-propyl, or i-propyl substituents, or $R^7$ and $R^8$, together with the nitrogen atom to which they are attached, represent a 5- to 6-membered heterocycle selected from the series consisting of piperidino, morpholino, thiomorpholino, piperazino, pyrrolidino, oxazolidino, thiazolidino, 4H-1-oxazinyl, and 4H-1-thiazinyl, each of which is optionally substituted from one to four times by identical or different substituents selected from the group consisting of fluorine, chlorine, bromine, methyl, ethyl, n-propyl, i-propyl, n-butyl, i-butyl, s-butyl, t-butyl, methoxy, ethoxy, n-propoxy, i-propoxy, n-butoxy, i-butoxy, s-butoxy, t-butoxy, methylthio, ethylthio, n-propylthio, i-propylthio, n-butylthio, i-butylthio, s-butylthio, t-butylthio, $C_1$–$C_4$-haloalkyl, $C_1$–$C_4$-haloalkoxy, and $C_1$–$C_4$-haloalkylthio having in each case 1 to 9 fluorine, chlorine, and/or bromine atoms, wherein the piperazino radical is substituted on the second nitrogen atom by $R^9$, and $R^9$ represents hydrogen, methyl, ethyl, n-propyl, i-propyl, n-butyl, i-butyl, s-butyl, t-butyl, vinyl, or allyl.

8. A $\Delta^1$-pyrroline of formula (I) according to claim 7 in which $R^7$ and $R^8$ independently of one another represent methyl, ethyl, n-propyl, i-propyl, n-butyl, i-butyl, s-butyl, t-butyl, the isomeric pentyls, and the isomeric hexyls, each of which is optionally substituted one or more times by identical or different substituents selected from the group consisting of fluorine, chlorine, bromine, $C_1$–$C_4$-alkylcarbonyl, $C_1$–$C_4$-alkylcarbonyloxy, $C_1$–$C_4$-alkylamino, di-($C_1$–$C_4$-alkyl)amino, $C_1$–$C_{10}$-alkoxy, $C_1$–$C_8$-alkoxy-$C_1$–$C_6$-alkoxy, $C_1$–$C_{10}$-alkylthio, $C_1$–$C_{10}$-haloalkoxy, $C_1$–$C_{10}$-haloalkylthio having in each case 1 to 21 fluorine, chlorine and/or bromine atoms, $C_1$–$C_8$-haloalkoxy-$C_1$–$C_6$-alkoxy having 1 to 17 fluorine, chlorine and/or bromine atoms.

9. A $\Delta^1$-pyrroline of formula (I-1) or (I-2)

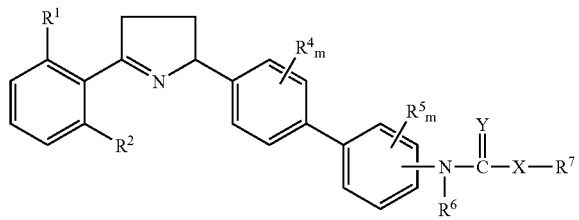

(I-1)

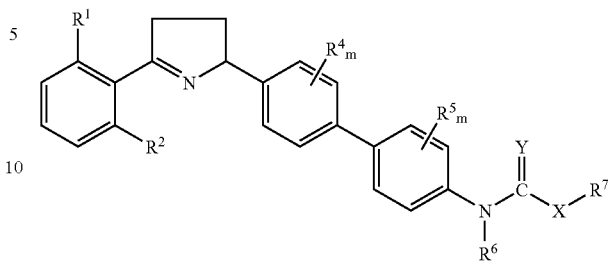

(I-2)

in each of which

Y represents O or S,

X represents O, S, or $NR^8$, $R^1$ represents halogen or methyl, $R^2$ represents hydrogen or halogen, $R^4$ and $R^5$ independently of one another represent halogen, alkyl, alkoxy, alkylthio, haloalkyl, haloalkoxy, or haloalkylthio, m represents 0, 1, 2, 3, or 4, $R^6$ represents hydrogen or alkyl, $R^7$ and $R^8$ independently of one another represent hydrogen; represent alkyl or alkenyl, each of which is optionally substituted one or more times by identical or different substituents selected from the group consisting of halogen, alkylcarbonyl, alkylcarbonyloxy, alkylamino, dialkylamino, alkoxy, alkylthio, alkoxyalkoxy, haloalkoxy, haloalkylthio, and halogenalkoxyalkoxy; or represent cycloalkyl, cycloalkylalkyl, aryl, arylalkyl, or saturated or unsaturated 5- to 10-membered heterocyclyl or heterocyclylalkyl, each of which is optionally substituted one or more times by identical or different substitutents selected from the group consisting of halogen, alkyl, haloalkyl, alkoxy, haloalkoxy, alkylthio, haloalkylthio, alkylcarbonyl. and alkoxycarbonyl, or $R^6$ and $R^7$ together represent alkylene optionally substituted one or more times by alkyl, or $R^7$ and $R^8$, together with the nitrogen atom to which they are attached, represent a saturated or unsaturated 5- to 10-membered heterocycle that optionally contains a further heteroatom group selected from the series —O—, —S—, and —$NR^9$— and that is optionally substituted one or more times by identical or different substituents selected from the group consisting of halogen, alkyl, alkoxy, alkylthio, haloalkyl, haloalkoxy, and haloalkylthio, and $R^9$ represents hydrogen, alkyl, or alkenyl.

10. A $\Delta^1$-pyrroline of formula (I) according to claim 1 in which A represents phenylene.

11. A $\Delta^1$-pyrroline of formula (I) according to claim 1 in which A represents 1,4-phenylene.

12. A $\Delta^1$-pyrroline of formula (I) according to claim 1 in which Y represents O.

13. A $\Delta^1$-pyrroline of formula (I) according to claim 1 in which X represents O or $NR^8$.

14. A $\Delta^1$-pyrroline of formula (I) according to claim 1 in which Y and X each represent O.

15. A $\Delta^1$-pyrroline of formula (I) according to claim 1 in which Y represents O and X represents $NR^8$.

16. A $\Delta^1$-pyrroline of formula (I) according to claim 1 in which $R^1$ and $R^2$ each represent fluorine.

17. A $\Delta^1$-pyrroline of formula (I) according to claim 1 in which $R^1$ represents methyl and $R^2$ represents hydrogen.

18. A Δ¹-pyrroline of formula (I) according to claim 1 in which R¹ represents chlorine and R² represents hydrogen.

19. A Δ¹-pyrroline of formula (I) according to claim 1 in which R¹ represents chlorine and R² represents fluorine.

20. A Δ¹-pyrroline of formula (I) according to claim 1 in which R⁶ represents hydrogen.

21. A Δ¹-pyrroline of formula (I-a) having (R) configuration in position 5 of the pyrroline ring

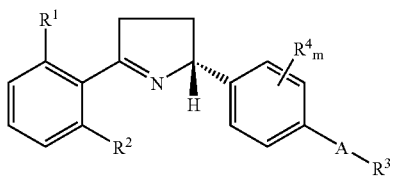
(I-a)

in which
- R¹ represents halogen or methyl,
- R² represents hydrogen or halogen,
- R³ represents —N(R⁶)—C(=Y)—X—R⁷,
- A represents arylene that is optionally substituted from one to four times by identical or different substituents R⁵,
- Y represents O or S,
- X represents O, S, or NR⁸,
- R⁴ and R⁵ independently of one another represent halogen, alkyl, alkoxy, alkylthio, haloalkyl, haloalkoxy, or haloalkylthio,
- m represents 0, 1, 2, 3, or 4,
- R⁶ represents hydrogen or alkyl,
- R⁷ and R⁸ independently of one another represent hydrogen; represent alkyl or alkenyl, each of which is optionally substituted one or more times by identical or different substituents selected from the group consisting of halogen, alkylcarbonyl, alkylcarbonyloxy, alkylamino, dialkylamino, alkoxy, alkylthio, alkoxyalkoxy, haloalkoxy, haloalkylthio, and halogenalkoxyalkoxy; or represent cycloalkyl, cycloalkylalkyl, aryl, arylalkyl, or saturated or unsaturated 5- to 10-membered heterocyclyl or heterocyclylalkyl, each of which is optionally substituted one or more times by identical or different substituents selected from the group consisting of halogen, alkyl, haloalkyl, alkoxy, haloalkoxy, alkylthio, haloalkylthio, alkylcarbonyl. and alkoxycarbonyl, or
- R⁶ and R⁷ together represent alkylene optionally substituted one or more times by alkyl, or
- R⁷ and R⁸, together with the nitrogen atom to which they are attached, represent a saturated or unsaturated 5- to 10-membered heterocycle that optionally contains a further heteroatom group selected from the series —O—, —S—, and —NR⁹— and that is optionally substituted one or more times by identical or different substituents selected from the group consisting of halogen, alkyl, alkoxy, alkylthio, haloalkyl, haloalkoxy, and haloalkylthio, and
- R⁹ represents hydrogen, alkyl, or alkenyl.

22. A process for preparing compounds of formula (I) according to claim 1 comprising
reacting a Δ¹-pyrroline of formula (II)

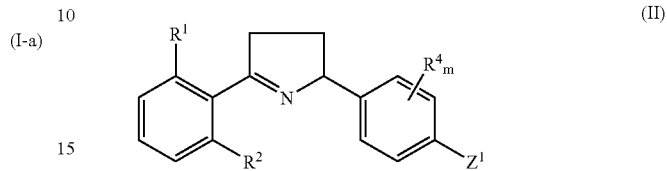
(II)

in which
R¹, R², R⁴, and m have the meanings given for formula (I) in claim 1, and
Z¹ represents chlorine, bromine, iodine, —OSO₂CF₃, or —OSO₂(CF₂)₃CF₃,
in a tandem reaction with a compound of formula (III)

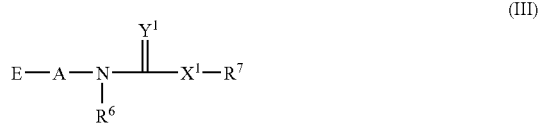
(III)

in which
A, R⁶, and R⁷ have the meanings given for formula (I) in claim 1,
Y¹ represents O,
X¹ represents O or NR⁸, and
E represents chlorine, bromine, iodine, —OSO₂CF₃, or —OSO₂(CF₂)₃CF₃,
in the presence of a palladium catalyst, in the presence of a diboronic ester, optionally in the presence of an acid binder, and optionally in the presence of a diluent.

23. A pesticide comprising at least one compound of the formula (I) according to claim 1 and one or more extenders and/or surface-active substances.

24. A method of controlling insects, arachnids, or nematodes comprising causing an effective amount of one or more compounds of formula (I) according to claim 1 to act on said insects, arachnids, or nematodes and/or their habitat.

25. A process for producing pesticides comprising mixing one or more compounds of formula (I) according to claim 1 with one or more extenders and/or surface-active substances.

* * * * *